United States Patent
Davis et al.

(10) Patent No.: US 9,692,839 B2
(45) Date of Patent: *Jun. 27, 2017

(54) CONTEXT EMOTION DETERMINATION SYSTEM

(71) Applicant: General Instrument Corporation, Horsham, PA (US)

(72) Inventors: Paul C. Davis, Arlington Heights, IL (US); Mir F. Ali, Rolling Meadows, IL (US); Jianguo Li, Chicago, IL (US); Dale W. Russell, Palatine, IL (US); Di You, Grayslake, IL (US)

(73) Assignee: ARRIS Enterprises, Inc., Suwanee, GA (US)

( * ) Notice: Subject to any disclaimer, the term of this patent is extended or adjusted under 35 U.S.C. 154(b) by 797 days.

This patent is subject to a terminal disclaimer.

(21) Appl. No.: 13/798,367

(22) Filed: Mar. 13, 2013

(65) Prior Publication Data

US 2014/0280529 A1 Sep. 18, 2014

(51) Int. Cl.
*G06F 17/27* (2006.01)
*H04L 29/08* (2006.01)
(Continued)

(52) U.S. Cl.
CPC ........ *H04L 67/22* (2013.01); *A61B 5/0022* (2013.01); *A61B 5/165* (2013.01); *G06F 17/27* (2013.01);
(Continued)

(58) Field of Classification Search
CPC ...... G06F 17/21; G06F 17/27; G06F 17/2785; G06F 2203/011
See application file for complete search history.

(56) References Cited

U.S. PATENT DOCUMENTS 7,856,360 B2 12/2010 Kramer et al.
7,921,067 B2 4/2011 Kemp et al.
(Continued)

FOREIGN PATENT DOCUMENTS

EP 2333778 A1 6/2011
WO 2012/019643 A1 2/2012

OTHER PUBLICATIONS

PCT Search Report & Written Opinion, Re: Application #PCT/US14/22887; dated Oct. 1, 2014.
(Continued)

*Primary Examiner* — Jeong S Park
(74) *Attorney, Agent, or Firm* — Stewart M. Wiener

(57) ABSTRACT

Systems, methods, and devices for determining contexts and determining associated emotion profiles using information received from multiple emotion sensor enabled electronic devices, are disclosed. Contexts can be defined by a description of spatial and/or temporal components. Such contexts can be arbitrarily defined using semantically meaningful and absolute descriptions of times and locations. Emotion sensor data is associated with or includes context data that describes the circumstances under which the data was determined. The emotion sensor data can include emotion sensor readings that are implicit indications of an emotion for the context. The sensor data can also include user reported data with explicit descriptors of an emotion for the context. The emotion sensor data can be filtered by context data according a selected context. The filtered sensor data can then be analyzed to determine an emotion profile for the context that can be output to one or more users or entities.

19 Claims, 18 Drawing Sheets

(51) Int. Cl.
*A61B 5/16* (2006.01)
*G06F 17/21* (2006.01)
*A61B 5/00* (2006.01)

(52) U.S. Cl.
CPC ........ *G06F 17/2785* (2013.01); *A61B 5/6898* (2013.01); *G06F 17/21* (2013.01); *G06F 2203/011* (2013.01)

(56) References Cited

U.S. PATENT DOCUMENTS

| | | | |
|---|---|---|---|
| 8,172,777 B2 | 5/2012 | Goto | |
| 8,239,774 B2 | 8/2012 | Gandhi et al. | |
| 8,255,240 B2 | 8/2012 | O'Hanlon et al. | |
| 8,255,392 B2 | 8/2012 | Melton | |
| 8,281,005 B2 | 10/2012 | Vanderhook et al. | |
| 2002/0046030 A1 | 4/2002 | Haritsa et al. | |
| 2006/0143647 A1* | 6/2006 | Bill | G06F 17/30743 725/10 |
| 2006/0195361 A1 | 8/2006 | Rosenberg | |
| 2009/0131764 A1 | 5/2009 | Lee et al. | |
| 2010/0145695 A1 | 6/2010 | Jung et al. | |
| 2010/0299615 A1 | 11/2010 | Miluzzo et al. | |
| 2010/0318576 A1 | 12/2010 | Kim | |
| 2010/0332288 A1 | 12/2010 | Higgins et al. | |
| 2011/0112825 A1* | 5/2011 | Bellegarda | G06F 17/2785 704/9 |
| 2011/0264531 A1* | 10/2011 | Bhatia | G06Q 30/0269 705/14.66 |
| 2011/0301433 A1 | 12/2011 | Sadowsky et al. | |
| 2012/0066302 A1 | 3/2012 | Petersen et al. | |
| 2012/0071175 A1 | 3/2012 | Skibiski et al. | |
| 2012/0072939 A1 | 3/2012 | Crenshaw | |
| 2012/0203081 A1 | 8/2012 | LeBoeuf et al. | |
| 2012/0226112 A1 | 9/2012 | LeBoeuf et al. | |
| 2012/0312872 A1 | 12/2012 | Clapsaddle | |
| 2013/0019187 A1* | 1/2013 | Hind | H04L 65/4023 715/753 |
| 2013/0030931 A1* | 1/2013 | Moshfeghi | G01S 19/48 705/16 |
| 2013/0036080 A1 | 2/2013 | Kane-Esrig | |
| 2013/0103637 A1 | 4/2013 | Dror et al. | |
| 2013/0152000 A1* | 6/2013 | Liu | G06F 9/44 715/765 |
| 2013/0325437 A1* | 12/2013 | Lehman | G06F 17/2785 704/9 |
| 2014/0025620 A1* | 1/2014 | Greenzeiger | G06F 17/30702 706/47 |
| 2014/0040171 A1 | 2/2014 | Segalov et al. | |
| 2014/0089399 A1* | 3/2014 | Chun | G06Q 50/01 709/204 |
| 2014/0266782 A1 | 9/2014 | You et al. | |
| 2014/0280138 A1* | 9/2014 | Li | G06Q 30/02 707/737 |
| 2014/0350349 A1* | 11/2014 | Geurts | A61B 5/0022 600/300 |

OTHER PUBLICATIONS

PCT Search Report & Written Opinion, Re: Application #PCT/US2014/022886; dated Jun. 17, 2014.
E. Bozkurt, et al., "Improving Automatic Emotion Recognition from Speech Signals", 10th Annual Conference of the International Speech Communication Association, 2009, 4 pages.
A. Haag, et al., "Emotion Recognition Using Bio-Sensors: First Steps Towards an Automatic System", Affective Dialogue Systems, 3068:, 2004, pp. 36-48.
J. Bailenson, et al., "Real-time classification of evoked emotions using facial feature tracking and physiological responses", International Journal of Human-Computer Studies, 66:, 2008, pp. 303-317.
C. Chang, et al., "Application of support vector regression for physiological emotion recognition", in International Computer Symposium, 2010.
G. Wu, et al., "The analysis of emotion recognition from GSR based on PSO", in International Symposium on Intelligence Information Processing and Trusted Computing, 2010.
E. Howarth, et al., "A multidimensional approach to the relationship between mood and weather", British Journal of Psychology, 75:, 1984, pp. 15-23.
R. Picard, et al., "Toward Machine Emotional Intelligence: Analysis of Affective Physiological State", IEEE Transactions on PAMI, 2001, pp. 1-24.
J. Hernandez, et al., "Mood Meter: Counting Smiles in the Wild", UBICOMP, Sep. 2012, 10 pages.
J. Hernandez, et al., "Mood Meter: Large-Scale and Long-Term Smile Monitoring System", ACM SIGGRAPH Emerging Technologies, Aug. 2012.
E. Miluzzo, et al., "Sensing Meets Mobile Social Networks: The Design, Implementation and Evaluation of the CenceMe Application", Proceedings of the 6th ACM conference on Embedded network sensor systems, Nov. 5-7, 2008, pp. 337-350.
E. Miluzzo, et al., "Tapping into the Vibe of the City Using VibN, a Continuous Sensing Application for Smartphones", Proceedings of 1st International Symposium on From digital footprints to Social and Community Intelligence, Sep. 18, 2011, 6 pages.
K. Rachuri, et al., "EmotionSense: A Mobile Phones based Adaptive Platform for Experimental Social Psychology Research", Ubicomp '10: Proceedings of the 12th ACM international conference on Ubiquitous computing, Sep. 26-29, 2010, 10 pages.
R. Likamwa, et al., "Can Your Smartphone Infer Your Mood?", PhoneSense Workshop, 2011, pp. 1-5.
K. Chang, et al., "Speech Analysis Methodologies Towards Unobtrusive Mental Health Monitoring", Technical Report No. UCB/EECS-2012-55, May 1, 2012, 120 pages.
J. Biswas, et al., "Health and wellness monitoring through wearable and ambient sensors: exemplars from home-based care of elderly with mild dementia", Annals of Telecommunications, 65(9):505-521, 2012.
M. Alwan, "Passive in-home health and wellness monitoring: overview, value and examples", Conf Proc IEEE Eng Med Biol Soc, 2009.
R. Shahriyar, et al., "Intelligent Mobile Health Monitoring System (IMHMS)", International Journal of Control and Automation, 2:3, 2009.
J. Tielsch, "Public Health Surveillance: Methods and Application", 2004.
P. Nsubuga, et al., "Public Health Surveillance: A Tool for Targeting and Monitoring Intervention", Disease Control Priorities in Developing Countries. 2nd edition, 2006.
K. Buchin, "Processing aggregated data: the location of clusters in health data", Journal Geoinformatica, 16(3): 497-521, 2012.
J. Luck, "Using Local Health Information to Promote Public Health", Health Aff (Millwood), 25(4):979-991, 2006.
Nike, Inc., "RUNCHI Chicago Showdown" (n.d.), accessed Oct./Nov. 2012.
L. Moncur, "Pick a 'Hood", Starling Fitness: Daily Writings on Fitness, Diet, and Health (weblog), Jun. 10, 2007. URL: http://www.starling-fitness.com/archives/2007/06/10/pick-a-hood/.
Centers for Disease Control and Prevention (CDC), "Obesity and Overweight for Professionals: Data and Statistics: Adult Obesity—DNPAO—CDC", dated Aug. 13, 2012, archived Sep. 16, 2012. URL: web.archive.org/web/20120916112915/http://www.cdc.gov/obesity/data/adult.html.
MapMyFitness, Inc., "Fittest of the Fit Index", dated May 2012, archived Jul. 14, 2012. URL: web.archive.org/web/20120714013919/http://www.mapmyfitness.com/intel/fittest_of_the_fit/.
Official Action, Re: Canadian Application No. 2,902,521, dated Sep. 19, 2016.
Official Action, Re: Korean Application No. 10-2015-7024724, dated Nov. 8, 2016.

* cited by examiner

CONTEXT EMOTION DETERMINATION SYSTEM

BACKGROUND

Various types of devices, sensors and techniques exist for determining implicit and explicit characteristics of people and places. Some systems use devices associated with a particular user to sense or determine user specific information. Sensors in or coupled to a mobile electronic device can sense various implicit indicators of characteristics for a particular user. For example, sensors in a smartphone can sense the physical properties, e.g., position, temperature, rate of motion, heartbeat, etc., of a particular user of the device to gather information that can imply characteristics for that particular user. Other conventional mobile electronic device based systems also gather information about particular users by providing mechanisms through which a user can explicitly report user characteristics, e.g., age, mood, state of health, weight, etc. For example, a smartphone can execute an application that prompts a user to explicitly enter personal information. These types of mobile electronic devices only gather information for one user at a time. That is, typically, each mobile electronic device only gathers information about the owner or the current user of the device.

Other systems use stationary sensors, such as cameras, infrared imagers, microphones, voice recognition, etc., to detect the characteristics of multiple people in a particular area in proximity to the sensors. Such systems can analyze the physical properties of the people to determine characteristics, e.g., mood, health, or demographic information, for the people in that particular location. For example, systems exist that can determine the mood, e.g., happy, content, sad, etc., of some portion of the people in a location based on the physical properties, such as the degree to which a person is smiling, for people who come within range of a particular sensor. Because the sensors in such systems are stationary, the results are limited to locations in which the sensors are installed. Furthermore, the resulting sample of a particular group or population within range of the sensors is limited. The limited sampling of the group of people can skew the results when interpolating, or otherwise determining, the mood or other characteristics associated with a given location.

FIG. 1 illustrates a diagram of a particular region 100. The region 100 can include a number of locations 120 in which various numbers of people 110 can be found. Some of the locations 120 can include a stationary sensor (SS) 115. As shown, the distribution of the stationary sensors 115 is limited to only a few of the possible locations 120. Accordingly, only locations 120 that include a stationary sensor 115 are capable of determining even an approximation of a characteristic, such as the mood, of some group of people 110 in a particular location 120 or region 100. In the specific example shown, only locations 120-1, 120-4, 120-6, 120-10, and 120-12 include stationary emotion sensors 115. The other locations 120 have no means for reliably determining the characteristics for those locations.

Furthermore, even locations 120 that are equipped with a stationary sensor 115 are limited by the ability of the sensor to detect only a limited sample of the people 110 in the location. The limits of the stationary sensors 120 can be based on the limits of the sensor in terms of range, speed, and accuracy. In addition, some people may actively avoid the stationary sensors 120. For instance, a mood detecting camera can be positioned at the front door of a given entertainment venue to capture the facial expressions of people as they enter the venue, and another mood detecting camera can be positioned near the performance stage of the same venue to capture facial expressions of people as they watch a performance. The facial expressions captured by the mood detecting camera at the front door of the venue might detect that a majority of the people entering the venue are excited, and the facial expressions captured by the mood detecting camera at the stage might detect that the majority of people near the stage are happy. However, there may be other people, or even a majority of people in the venue who may be bored, tired, or unhappy with the entertainment or the venue, but the mood detecting cameras cannot capture an image of them. In such situations, any interpolated result or conclusion as to the overall mood of the people in the venue can be spurious, and thus, not represent the true mood or success of the venue in entertaining its patrons.

DETAILED DESCRIPTION

Figure 1:
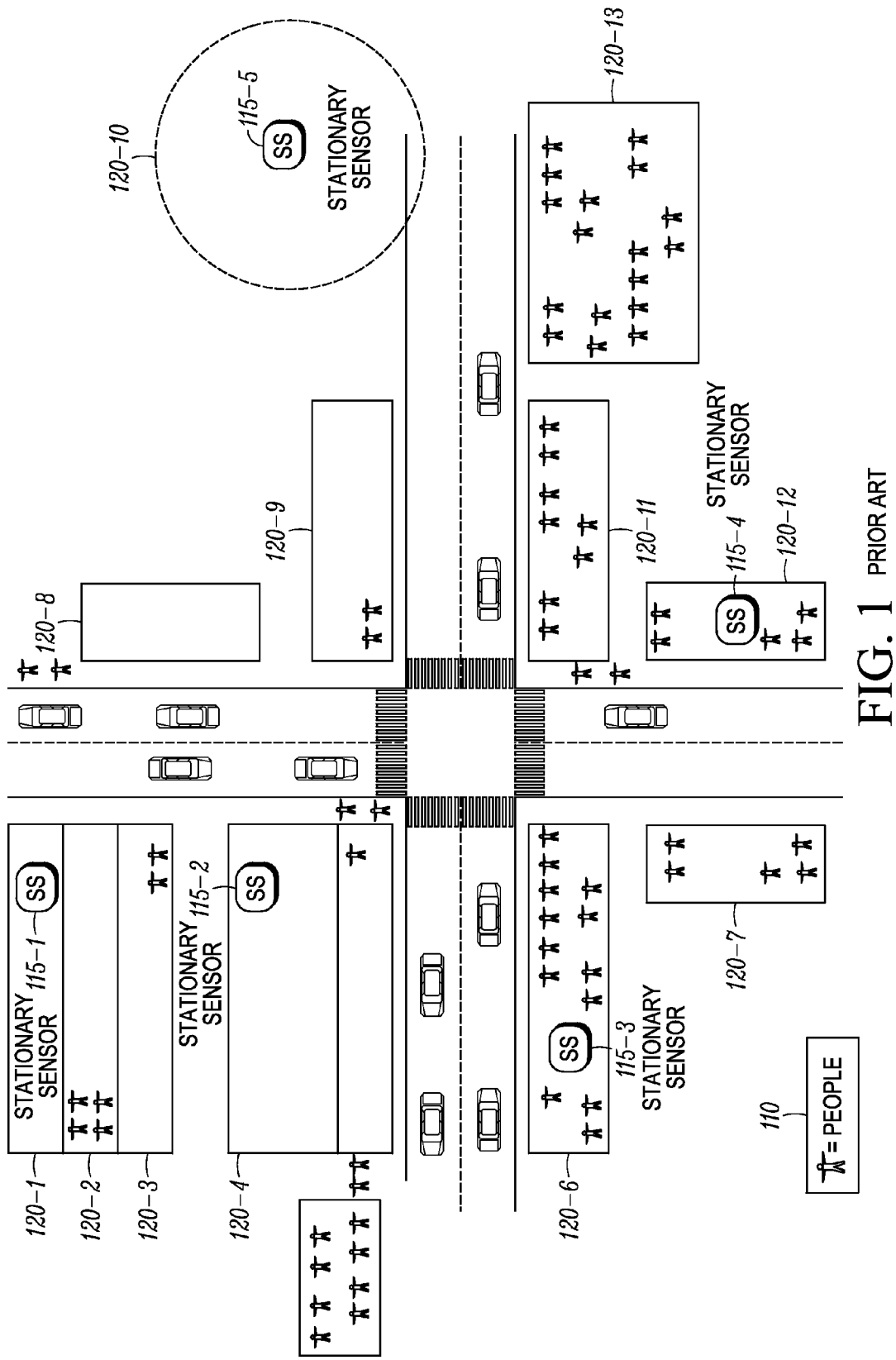
FIG. 1 illustrates conventional systems that use stationary sensor enabled electronic devices for determining limited characteristics for select contexts.

Described herein are techniques for systems and methods for flexibly defining a particular context and determining a characteristic for that context using distributed sensor enabled electronic devices. In particular, embodiments of the present disclosure include determining an emotion for a context using emotion sensors in stationary electronic devices and mobile electronic devices. In the following description, for purposes of explanation, numerous examples and specific details are set forth in order to provide a thorough understanding of particular embodiments. Particular embodiments as defined by the claims may include some or all of the features in these examples alone or in combination with other features described below, and may further include modifications and equivalents of the features and concepts described herein.

Various embodiments of the present disclosure include methods that can include receiving emotion sensor data from multiple distributed emotion sensor enabled electronic devices. The emotion sensor data can be based on information sensed by the distributed electronic devices for a plurality of contexts. Such methods can include determining a first context from multiple contexts, determining a first portion of the emotion sensor data determined to be received from a portion of the distributed electronic devices, wherein the portion of the emotion sensor data is based on information sensed for the first context. The methods can also include determining a first emotion profile for the first context based on the first portion of the emotion sensor data, wherein the first emotion profile comprises a description of an emotion associated with the first context.

Other embodiments of the present disclosure include non-transitory computer-readable storage media containing instructions that, when executed, control a processor of a computer system to be configured for receiving emotion sensor data from multiple distributed electronic devices, wherein the emotion sensor data is based on information sensed by the plurality of distributed electronic devices for a plurality of contexts. Such embodiments may also include determining a first context from multiple contexts, determining a first portion of the emotion sensor data determined to be received from a first portion of the plurality of distributed electronic devices, wherein the first portion of the emotion sensor data is based on information sensed for the first context, and determining a first emotion profile for the first context based on the first portion of the emotion sensor data. The first emotion profile may include a description of an emotion associated with the first context.

Various other embodiments of the present disclosure include an electronic device that includes a processor, an emotion sensor, an electronic communication interface, and a non-transitory computer-readable storage medium. The non-transitory computer-readable storage medium can contain instructions that when executed, control the processor to be configured to activate the emotion sensor to determine an emotion sensor reading, and determine context data for the emotion sensor reading. The context data describes the circumstances in which the emotion sensor reading was determined. The instructions can further control the processor to be configured to generate emotion sensor data that includes the context data and the emotion sensor reading, send the emotion sensor data to one or more remote service providers through the electronic communication interface, and receive, from a first remote service provider in the one or more remote service providers through the electronic communication interface, summary emotion sensor data for a particular context. The summary emotion sensor data may include emotion sensor data, received by the first remote service provider from a plurality of other electronic devices, and determined to include context data that matches the particular context.

Various embodiments of the present disclosure include systems, methods, and devices for determining contexts and determining an emotion or an emotion profile for those contexts using information received from multiple emotion sensor enabled electronic devices. Contexts can be defined by a description that includes spatial and/or temporal components. The spatial components can refer to various types of absolute and relative location description systems, such as coordinate based maps systems and proximity based location services. The temporal components can reference absolute and relative time description systems. Such time description systems can include a start time and date, a stop time and date, or a designation of some particular time period within some proprietary or universal time keeping system. In some embodiments, the context can be determined by the presence, concentration, or availability of emotion sensor data for a particular time and place. Accordingly, contexts can be arbitrarily defined as individual and composite combinations of time and location.

Once the context is selected or defined, all or some of the emotion sensor data received from multiple electronic devices can be filtered or analyzed to determine some portion of the emotion sensor data that includes or is associated with context data that matches the selected context. The context data can include temporal and spatial components that can describe the circumstances under which emotion sensor readings included in the sensor data were sensed, recorded, or otherwise determined. In some embodiments, the emotion sensor data can include implicit indications of emotion and explicit descriptors of emotions. The implicit descriptors can include processed or unprocessed emotion sensor readings. Such sensor readings can be mapped to a particular emotion or emotion profile. The explicit emotion descriptors can include one or more user reported points of data regarding a specific or general emotional state for a context, e.g., an emotional state reported by a user through a particular application, website, or social media network. As used herein, the term "emotion sensor" can refer to any sensor that may be used to sense information that can be used to infer an emotion or an emotion characteristic, regardless of quality or accuracy. For example, an accelerometer might be used to indicate the emotion of a person, or might be used in conjunction with the data from other sensors to infer emotion of one or more people.

The emotion sensor data determined to be received from emotion sensor enabled electronic devices that are or were in the context of interest can be analyzed to determine an emotion profile for the context. There are many forms that the resulting emotion profiles can take and can be based on the needs of the users or entities that will be consuming or viewing the emotion profiles. For example, the emotion profile can include a complete listing of all emotion sensor data for the context. In other embodiments, the emotion profile can include summaries of the most frequent emotion indicators and descriptors in the sensor data for the context. In one embodiment, the emotion profile can include an aggregation of all of the emotion indicators into a single, aggregate emotion indicator. Regardless of the format of the emotion profile, the profiles can be output over various channels and lines of communications. For example, the emotion profiles and the related contexts can be published to a website, sent as an email, broadcast in text messages, or pushed using a Really Simple Syndication (RSS) feed.

Various embodiments of the present disclosure will now be described in more detail with reference to specific devices, systems, and use cases.

Sensor Enabled Devices

Figure 2A:
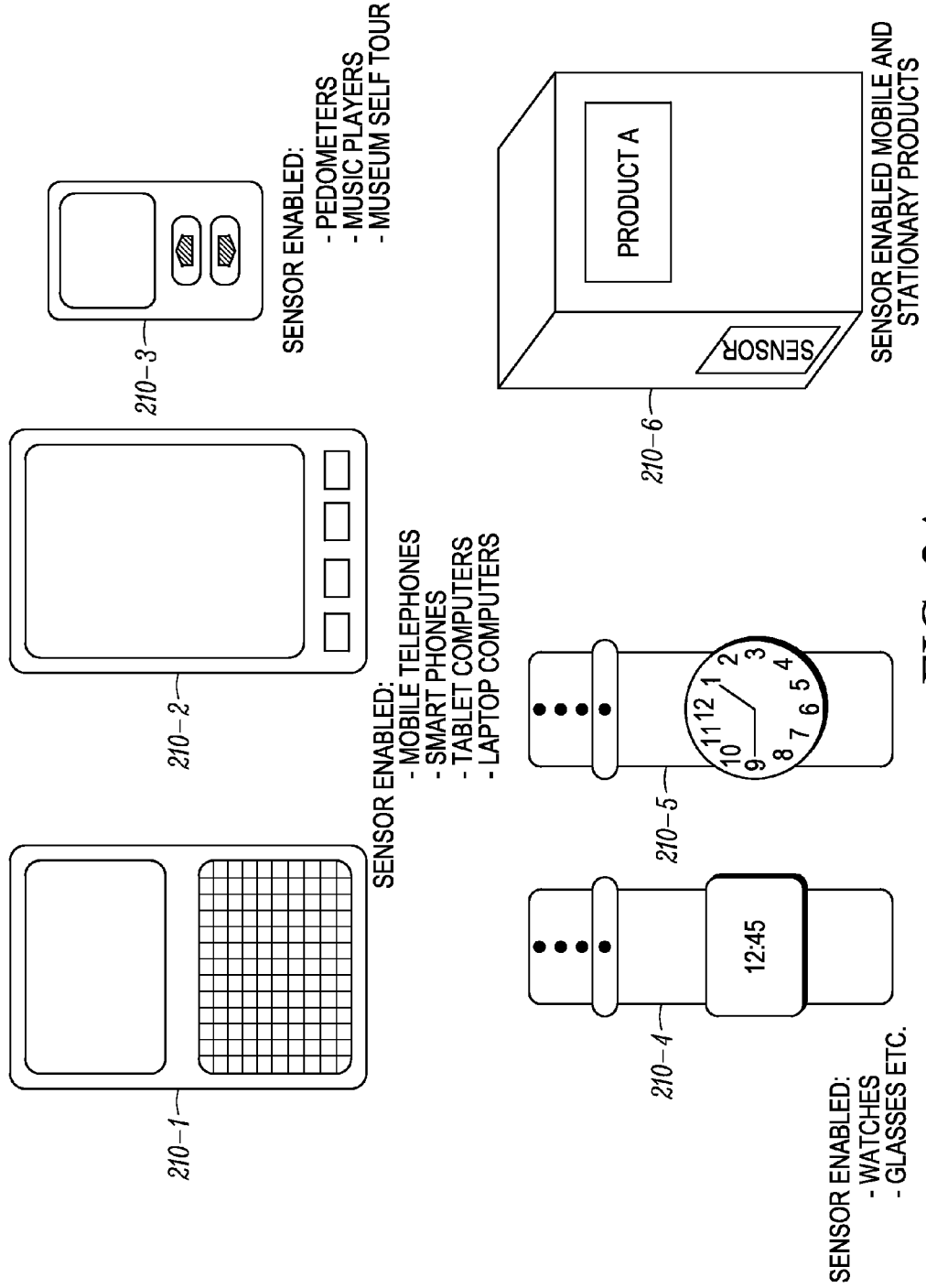
FIG. 2A illustrates various types of sensor enabled electronic devices that can be used in various embodiments of the present disclosure.

A significant portion of users encounters or uses at least one electronic device on a daily basis. Any or all such devices can be configured to include one or more varieties of sensors. FIG. 2A illustrates several examples of sensor enabled electronic devices 210. Some sensor enabled devices 210 are mobile devices (referred to as sensor enabled mobile electronic devices 210) that many users carry nearly every day. These devices include various types and brands of sensor enabled mobile telephones 210-1, smart phones 210-2, tablet computers, and laptop computers, etc. While mobile computing and communication devices are some of the most commonly used devices, there are other sensor enabled mobile electronic devices 210 that are also often used. For instance, various users carry sensor enabled pedometers, electronic music players (e.g., MP3) 210-3, watches 210-4, glasses, and, on occasion, specialty mobile electronic devices, like self-guided position-sensitive museum tour devices. In addition, there are configurations of mobile electronic devices in which one device can be tethered to or connected to another device. For example, a watch 210-4 or watch 210-5, can be connected to a smart phone 210-2 by a wired or wireless connection to share information, computing, networking, or sensor resources.

Any of the coupled or individual sensor enabled mobile electronic devices 210 may include one or more types of sensors, such as environmental, body, or location sensors. The mobility of such devices provides for flexible deployment of sensors into a wide range of contexts to determine various characteristics about those contexts. In addition, there may be some contexts that are equipped with one or more types of sensor enabled stationary devices (referred to as sensor enabled stationary electronic devices 210), shown generically at 210-6, that can be installed or placed in various contexts for detecting physical properties, e.g., temperature signatures, sound levels, facial expressions, etc., of people and conditions in those contexts. The information determined or sensed by stationary electronic devices 210-6 can be used independently or in conjunction with the information collected from other mobile and stationary sensor enabled devices.

Figure 2B:
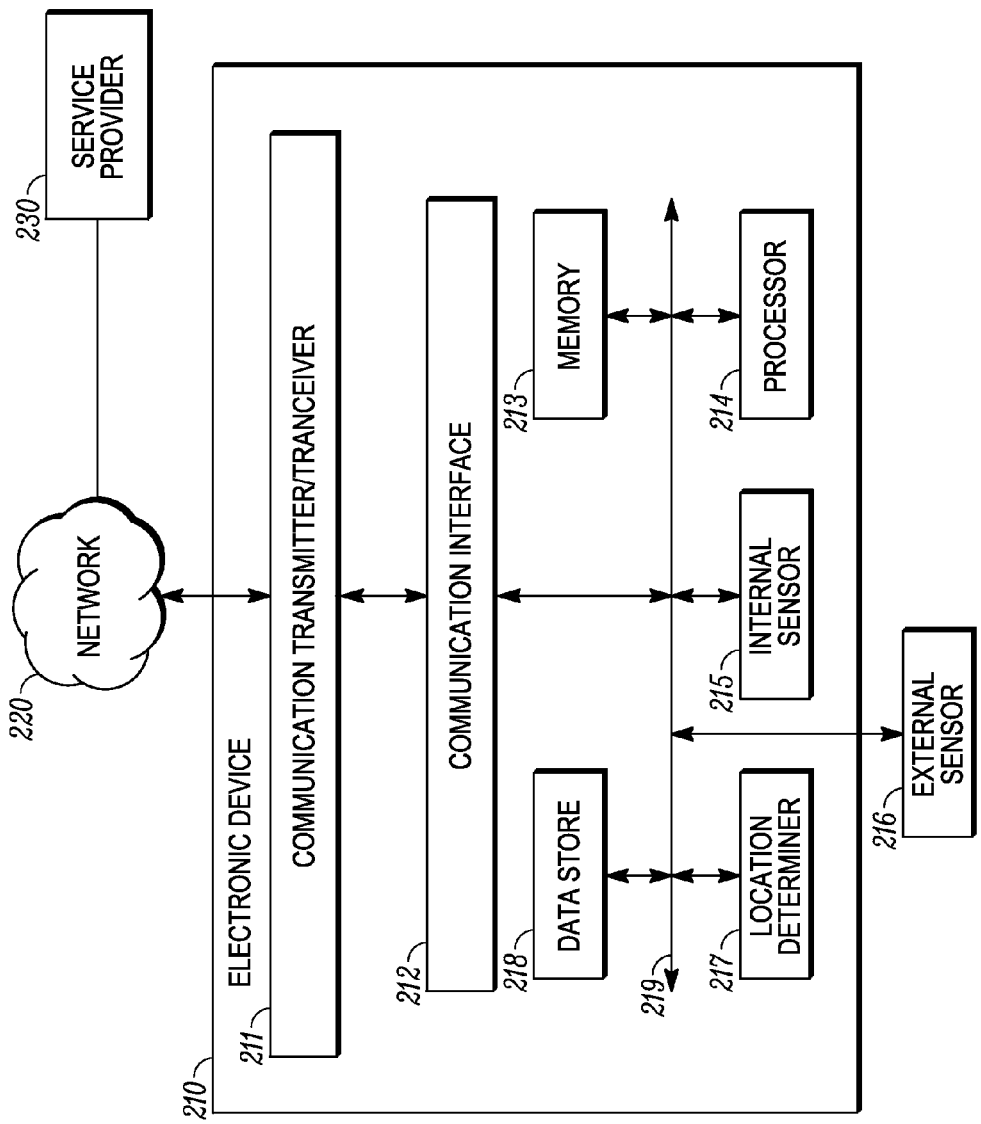
FIG. 2B is a block diagram of the sensor enabled electronic device that can be used in various embodiments of the present disclosure.

FIG. 2B illustrates a schematic of a sensor enabled electronic device 210 that can be used in implementations of various embodiments of the present disclosure. As discussed above, sensor enabled electronic device 210 can be a mobile or a stationary device. Either type of electronic device can include an internal communication bus 219, through which the constituent components of the electronic device 210 can communicate with and/or control one another. In some embodiments, electronic device 210 can include an internal sensor 215 and/or an external sensor 216. The sensors can include any type of sensor capable of detecting a physical characteristic of a person, object, or environment. In some embodiments, the external sensor 216 can be coupled to the electronic device 210 by a wired or wireless connection. Accordingly, the external sensor 216 can be configured to sense a region, object, or a part of a user's body that is separate from the electronic device 210. For example, the external sensor 216 can be included in a wrist watch, a pair of spectacles/goggles, or a body monitor that can be attached or affixed to a part of the user's body, e.g., a thermometer or heart rate monitor.

Each of the sensors can be controlled by the processor 214 executing computer readable code loaded into memory 213 or stored in the non-transitory computer readable medium of data store 218. Readings sensed by the external sensor 216 and internal sensor 215 can be collected by the processor 214 and stored locally in the memory 213 or the data store 218. In some embodiments, the readings from the external sensor 216 and/or the internal sensor 215 can be sent to remote service provider 230. In such embodiments, electronic device 210 can include a communication interface 212 for translating or converting the readings from the sensors from one format to another for transmission using the communication transmitter/transceiver 212 and network 220. Accordingly, electronic device 210 can be configured to communicate with network 220 and service provider 230 using a variety of wired and wireless electronic communication protocols and media. For example, electronic device 210 can be configured to communicate using Ethernet, IEEE 802.11xx, worldwide interoperability for my quick access (WiMAX), general packet radio service (GPRS), enhanced data rates for GSM evolution (EDGE), and long-term evolution (LTE), etc. The readings from the sensors, or sensor data that includes or is generated using the sensor readings, can be sent to the service provider 230 in real time. Alternatively, sensor readings or sensor data can be stored and/or sent to the service provider 230 in batches or as network connectivity allows.

In some embodiments, the sensor enabled electronic device 210 can also include a location determiner 217. The location determiner 217 can, through various methods and technologies, e.g., global positioning systems (GPS), near field communication (NFC), proximity sensors, etc., determine the location and movement of electronic device 210. In some embodiments, the location determined by the location determiner 217 can be included or associated with sensor readings from the external sensor 216 and/or the internal sensor 215 in sensor data sent to service provider 230. As used herein, the term sensor data is used to describe any data that includes or is associated with sensor readings and/or user reported data. For example, in some embodiments, sensor data can include the sensor readings and user reported data, along with the time, date, and location at which the sensor readings were taken or the user reported data was collected. The sensor data can also include any other conditions or exceptions that were detected when the corresponding sensor data was determined.

Deployment of Sensor Enabled Devices

Figure 3:
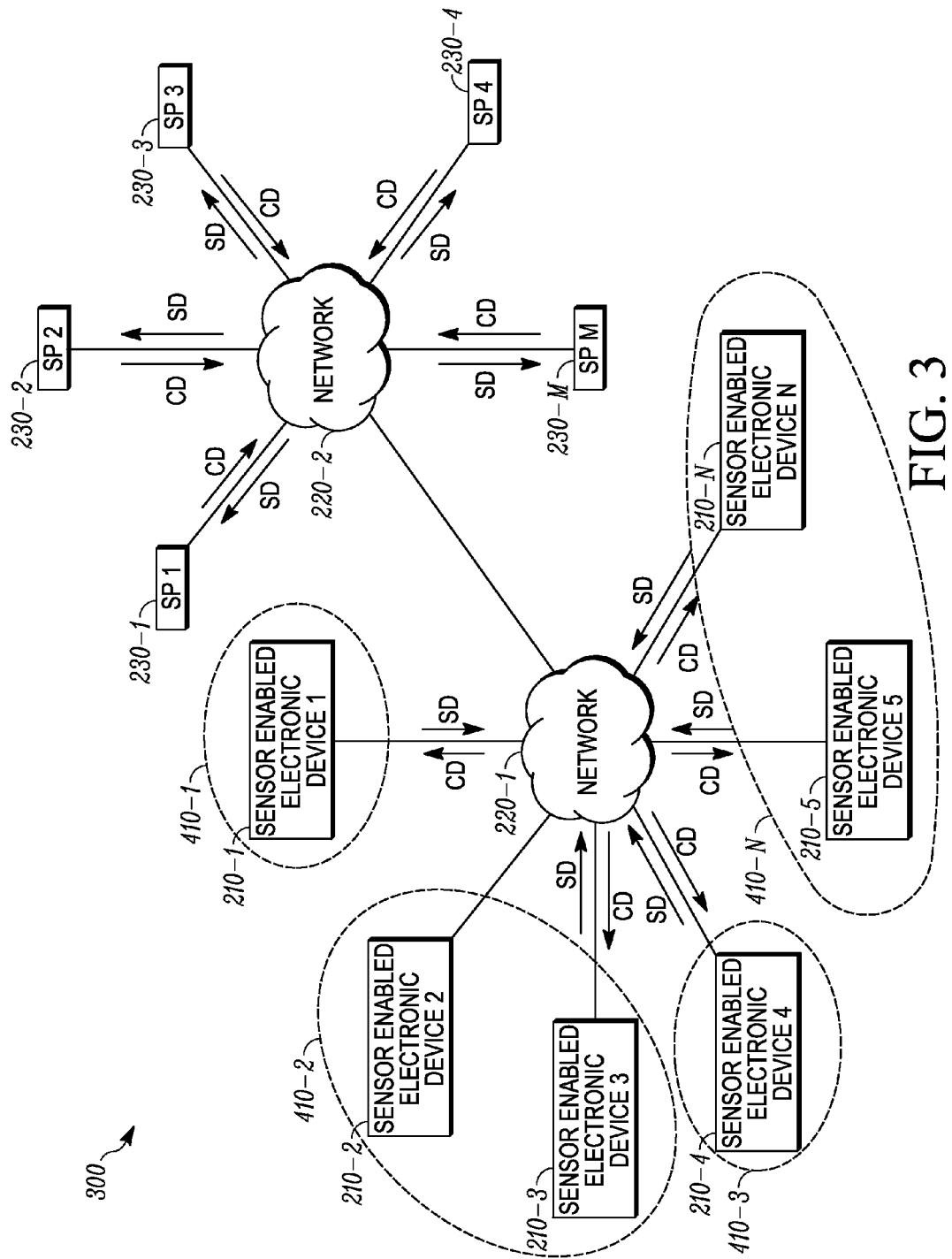
FIG. 3 is a block diagram of a system for the deployment of multiple stationary and mobile sensor enabled electronic devices for determining characteristics of various contexts, according to various embodiments of the present disclosure

FIG. 3 illustrates a schematic of a system 300 that includes many sensor enabled electronic devices 210 deployed in multiple contexts 410. The sensor enabled electronic devices 210 can be implemented as stationary or mobile devices. As such, the stationary devices can be explicitly associated with a particular location or event. For example, sensor enabled electronic device 210-1 can be a stationary device equipped with a camera, or other sensor, installed in a specific context, 410-1, such as a particular location or in a particular vehicle (e.g., a bus, train, plane, ship, or other multi-person conveyance).

In another example, some sensor enabled electronic devices 210 can be deployed passively. For example, sensor enabled mobile devices 210 can be passively deployed into multiple contexts by simply observing where users take their associated mobile devices. Passive deployment of the sensor enabled electronic devices 210 refers to the manner in which the devices are carried with users into whatever context the users choose. Accordingly, there is no central entity that is directing where each sensor enabled mobile electronic device 210 will be located or where it will go next. That decision is left up to individual users of the sensor enabled mobile electronic devices 210. Accordingly, sensor enabled mobile electronic devices 210-2 and 210-3 can be observed to be in a particular context 410-2, such as a location, at one time, but can then be observed in a different location at another time. Various advantages that can be realized due to the passive deployment of many sensor enabled mobile devices 210 will be described in reference to various examples below.

In some embodiments, each sensor enabled electronic device 210 may include one or more sensors or measurement devices for detecting, recording, or analyzing the characteristics of one or more users, locations, or time periods. For example, each sensor enabled electronic device 210 can include a light sensor, a microphone, decibel meter, an accelerometer, a gyroscope, a thermometer, a camera, an infrared imager, a barometer, an altimeter, a pressure sensor, a heart rate sensor, a galvanic skin response sensor, a vibration sensor, a weight sensor, an odor sensor, or any other specialized or general purpose sensor to detect characteristics of a particular user of a particular device or other users, areas, or objects in the vicinity of the device. As discussed above, the sensor enabled electronic devices 210 can also include location determination capabilities or functionality, e.g., a global positioning system (GPS), proximity detection, or Internet Protocol (IP) address location determination capabilities. In such embodiments, sensor data collected by the various sensors can be associated with a particular user and/or the particular location in which the sensor data was recorded or otherwise determined. In one embodiment, the sensor data can also include time and/or date information to indicate when the sensor data was captured or recorded. As used herein, any data referring to time, date, location, events, and/or any other spatial or temporal designation, can be referred to as context data. Accordingly, any particular sensor data can be associated with and/or include context data that describes the circumstances under which the sensor data was determined.

As shown in FIG. 2B, each of the sensor enabled electronic devices 210 can also include electronic communication capabilities. Accordingly, the sensor enabled electronic devices 210 can communicate with one another and various service providers 230 over one or more electronic communication networks 220 using various types of electronic communication media and protocols. The sensor enabled electronic devices 210 can send, and the service providers 230 can receive, sensor data (SD) associated with various particular users and contexts. The service providers 230, using one or more computer systems, can analyze the sensor data to determine a characteristic of a particular context.

In various embodiments of the present disclosure, the various service providers 230 can analyze the sensor data to determine mood, health, well-being, demographics, and other characteristics of any particular context 410 for which the service providers have sensor data. The service providers may then broadcast or selectively send the determined characteristics data (CD) for a particular context 410 to one or more of the sensor enabled electronic devices 210, as well as to other consumers. Such embodiments will be described in more detail below.

Determining Contexts

As discussed herein, context can be defined by a geographical area and time period at various levels of granularity. Accordingly, context can include predefined locations, such as a bar, restaurant, or amusement park during a particular predetermined time period or event. When using predetermined or physical locations, the address or other semantically meaningful designation of the location can be associated with a range of coordinates that are observable by the sensor enabled devices. In contrast, a context can be arbitrarily defined as any region or time period for which sensor data is available. For example, a service provider 230 can filter sensor data received from multiple sensor enabled electronic devices 210 for the sensor data associated with a specific context of interest, e.g., a specific neighborhood, street, park, theater, nightclub, vehicle, or event. Once the sensor data is filtered to isolate sensor data that includes context data that matches or is associated with specific context 410 that the service provider is interested in, the sensor readings in the sensor data can be analyzed to determine or interpolate a particular characteristic for that particular context 410.

Figure 4:
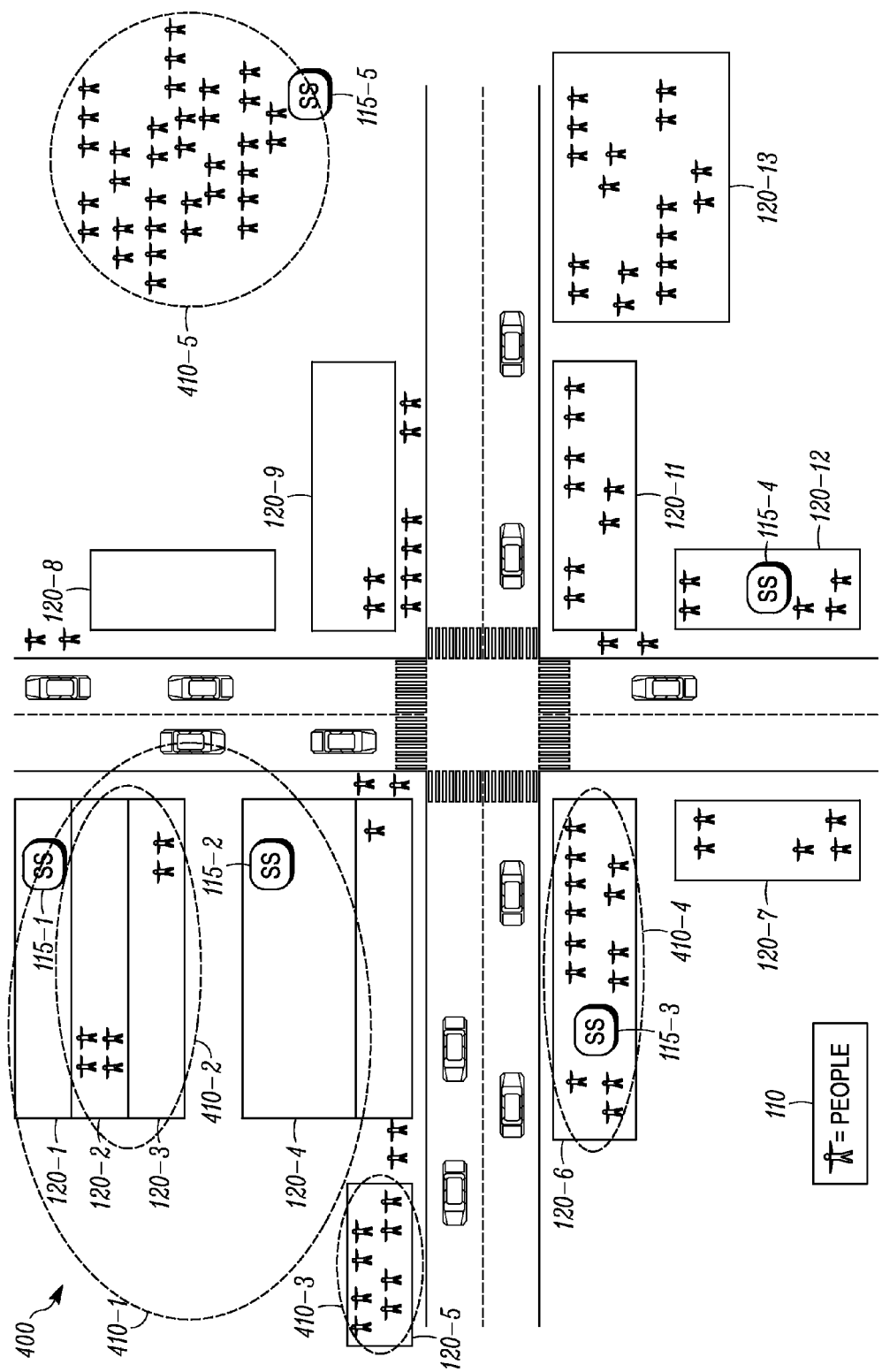
FIG. 4 illustrates various definitions of contexts, according to various embodiments of the present disclosure.

FIG. 4 illustrates how a region 400 can include a number of sub regions, or contexts 410, defined by a semantically meaningful geographic designation, like an address or venue name. As depicted, region 400 can be segmented into a number of physical locations 120 and contexts 410 by which the context data can be filtered or grouped. Area 400 may represent a city, a neighborhood, a business district, an amusement park, etc., or any sub region thereof. Region 400 can be further segmented into individual and composite contexts 410. For example, context 410-1 can include a city block of locations 120-1 through 120-5, e.g., a block of buildings or businesses, in a particular neighborhood of region 400. In some embodiments, each location 120-1 to location 120-5 can be a particular context. However, as shown, the context 410-1 can comprise all of the indoor space of locations 120-1 through 120-5, as well as any surrounding outdoor space, i.e., outside courtyards, sidewalks, and streets. Accordingly, by defining the area in and around locations 120-1 to 120-5 as a particular context 410-1, various representations about that context can be determined by analyzing the sensor data received from the sensor enabled devices determined to be in area 410-1. In one embodiment, a server computer of a service provider 230 can filter the sensor data by the GPS coordinates to determine which devices are or were in context 410-1. In other embodiments, the service provider may reference a semantically meaningful geographic location from social media check-in information included in the sensor data, e.g., a user may self-report that he or she is dining at a restaurant at location 120-1 or exercising at a gym 120-4 inside context 410-1.

As shown, context 410-1 can also include a number of sub-contexts, such as contexts 410-2 and 410-3 that can be defined by a physical location and time period. For example, context 410-2 can be defined by physical locations 120-3 and 120-3 between 9 am and 8 pm during some particular range of dates, e.g., a sale event. Similarly, context 410-3 can be defined by the physical location 120-5 on a specific night of a specific day of the year, e.g., a special event like a wedding or a concert. Using the definitions of the specific contexts of interest, particular embodiments can filter or sort the received sensor data to isolate and analyze the relevant sensor readings to make determinations about the characteristics of the people 110 in the particular contexts 410. For example, the sensor data for context 410-2 may indicate that the majority of the people in the context are "happy", while sensor data or user reported data for context 410-3 can indicate that the median age of the people in the context is 45 years old.

Similarly, context 410-4 can be defined to include location 120-6, the surrounding area of location 120-6, and the stationary sensor 115-3 on a particular night of the week, e.g., every Wednesday night. By including the stationary sensor 115-3, a server computer analyzing the sensor data from sensor enabled mobile electronic devices 210 associated with the people 110 in context 410-4 can incorporate sensor data from the stationary sensor 115-3. In such embodiments, the sensor data from sensor enabled mobile electronic devices 210 or the stationary sensor 115 can be weighted according to determined relevancy, reliability, recentness, or other qualities of the sensor data. Additionally, the relative weights of the sensor data received from the mobile and stationary devices can be based on predetermined thresholds regarding sample size. If sensor data is received from some threshold number of sensor enabled mobile electronic devices 210 in context 410-4, then the sensor data received from the stationary sensor 115-3 can have less weight in the conclusions about the characteristics of the context. In contrast, if only a few people in context 410-4 who are carrying sensor enabled mobile electronic devices 210 or there are only a few people in attendance, then the sensor data from stationary sensor 115-3 can be more heavily weighted. Sample size is just one example factor by which sensor data from mobile and stationary sensor enabled devices can be weighted relative to one another. Weighting sensor data according to various factors will be discussed below in more detail.

While the use of existing addresses and other semantically meaningful descriptions is a convenient way to define a particular context, some embodiments of the present disclosure allow for defining contexts that are not necessarily associated with a particular physical location 120, such as a building or a venue. For example, context 410-5 can be defined in an open space that may or may not include a stationary sensor 115-5. For example, context 410-5 can include a parking lot or municipal park with no definite physical boundaries. By filtering sensor data determined to include geographic information for a particular area of interest, particular embodiments can flexibly define contexts to include geographic locations of any size or shape. In some embodiments, the geographic locations in a particular context can be defined by a range of GPS coordinates.

Figure 5:
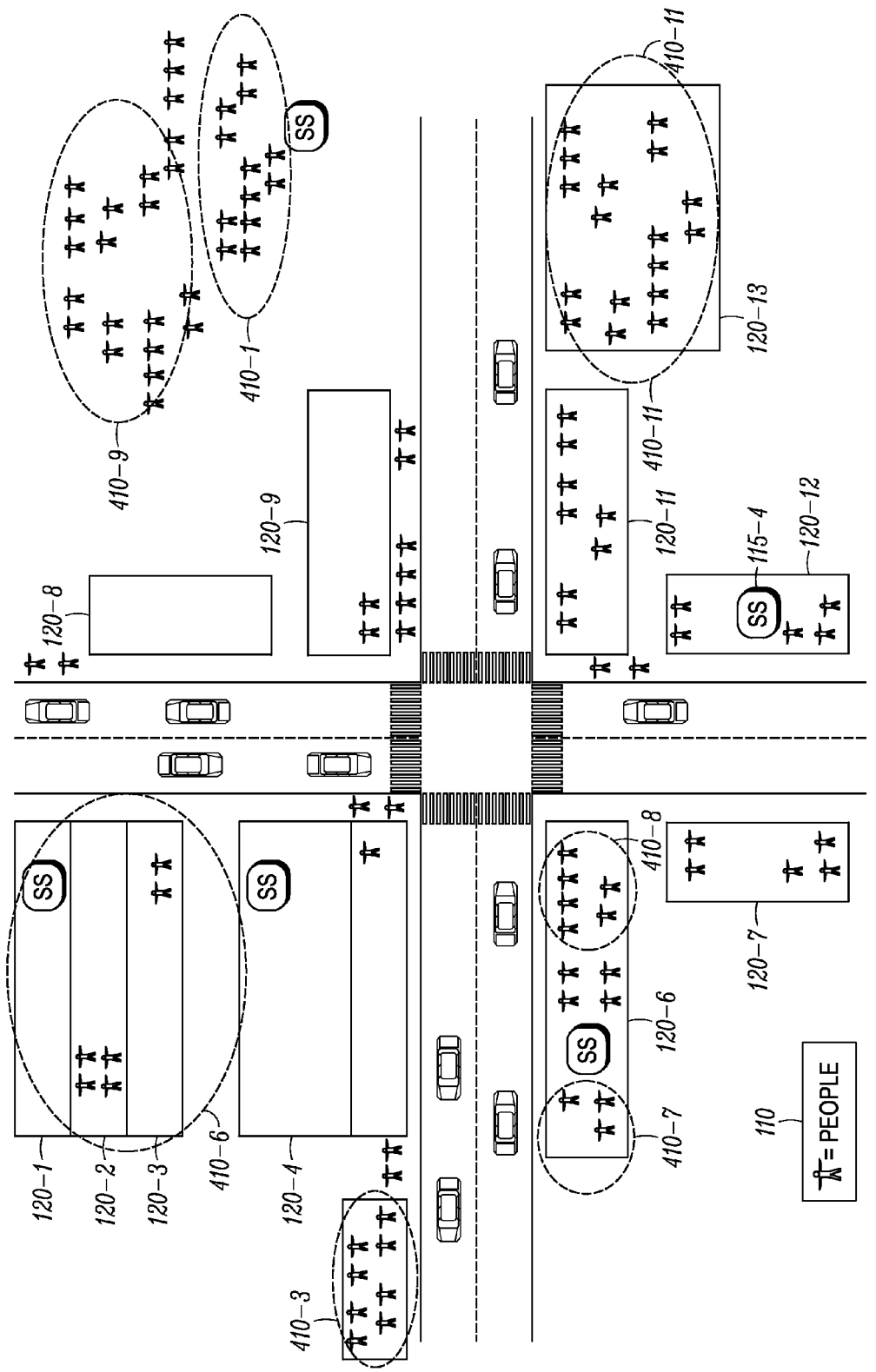
FIG. 5 illustrates the flexible definitions of contexts, according to various embodiments of the present disclosure.

Since a service provider can arbitrarily define a context, any previously defined context can be redefined at any time as needed. Accordingly, contexts 410-1 and 410-2 shown in FIG. 4 can be reduced/merged into context 410-6 show in FIG. 5. Similarly, context 410-5 shown in FIG. 4 can be divided into multiple contexts 410-9 and 410-10 as shown in FIG. 5 to obtain greater granularity in the sensor data associated with the larger context 410-5. For instance, the context 410-5 may originally have been defined around a large outdoor public space, but for a particular event, like a county fair or festival, may be divided to be centered around featured events or exhibits, such as a performance stage or art installation. Indoor spaces that define a context, such as location 120-6, which defined context 410-4 in FIG. 4, can also be divided into smaller contexts, like context 410-7 and 410-8 as shown in FIG. 5. In addition, new contexts can be added. Context 410-11 can be added in and around location 120-13 when a particular service provider or user requests or requires sensor data or a characteristic determination for that particular context. For example, a new restaurant or bar may have opened that an advertiser would like to know about.

Figure 6:
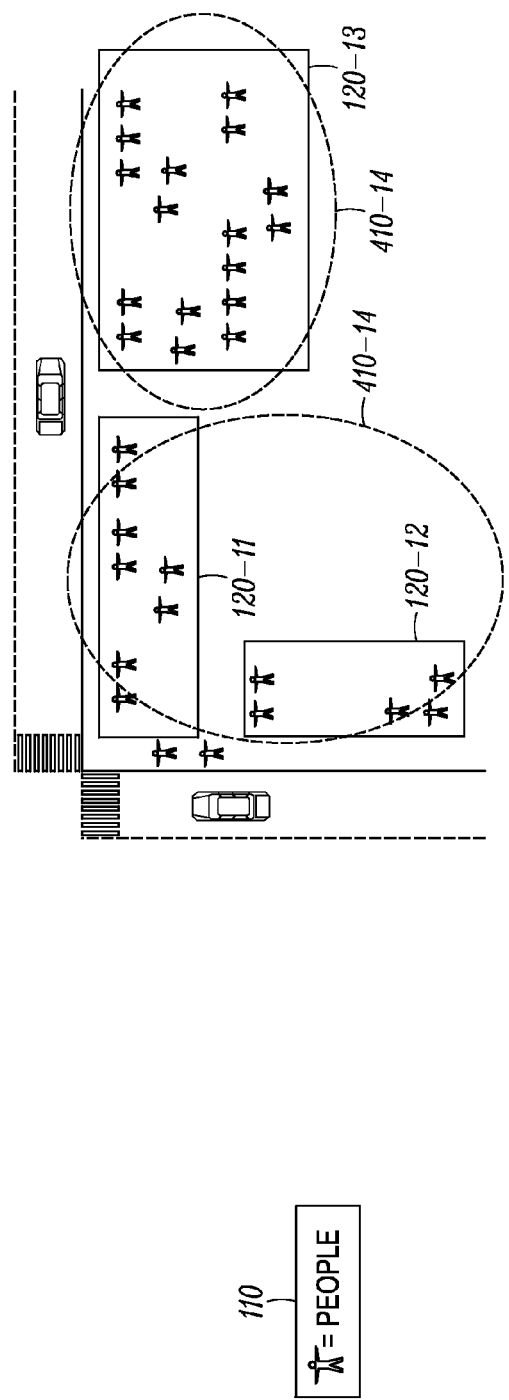
FIG. 6 illustrates the combination of spatial and temporal components in a context, according to various embodiments of the present disclosure.

As previously mentioned, the context can be defined by a combination of spatial and temporal coordinates. FIG. 6 illustrates one particular context 410-14 that may include designations of particular locations 120-11, 120-12, and 120-13, a particular day 615 of a particular month 610 at a particular time 620. As shown, context 410-14 can include any number of people 110 who may or may not be carrying one or more sensor enabled mobile electronic devices 210. Assuming that some portion of the people 110 are carrying sensor enabled mobile devices 210, then a service provider can receive sensor data for context 410-14. In some embodiments, the service provider can filter sensor data received from many sensor enabled mobile electronic devices 210 by analyzing the context data included in the sensor data to determine which sensor data is associated with or captured within the spatial and temporal boundaries of the context 410-14. For example, context 410-14 can include an event, e.g., a grand opening, occurring in multiple buildings 120-11, 120-12, and 120-13 on April 10, at 12:45 PM (−8 GMT). The service provider can then filter the sensor data for context data that matches the specific parameters with some degree of freedom, e.g., plus or minus 1 hour. The service provider can then analyze the sensor readings in the sensor data determined to match the specific parameters of the event to determine one or more characteristics of the event. While analysis of the sensor data for individual contexts is helpful for characterizing a particular context, it is often helpful or informative to understand how various characteristics change from context to context.

Figure 7:
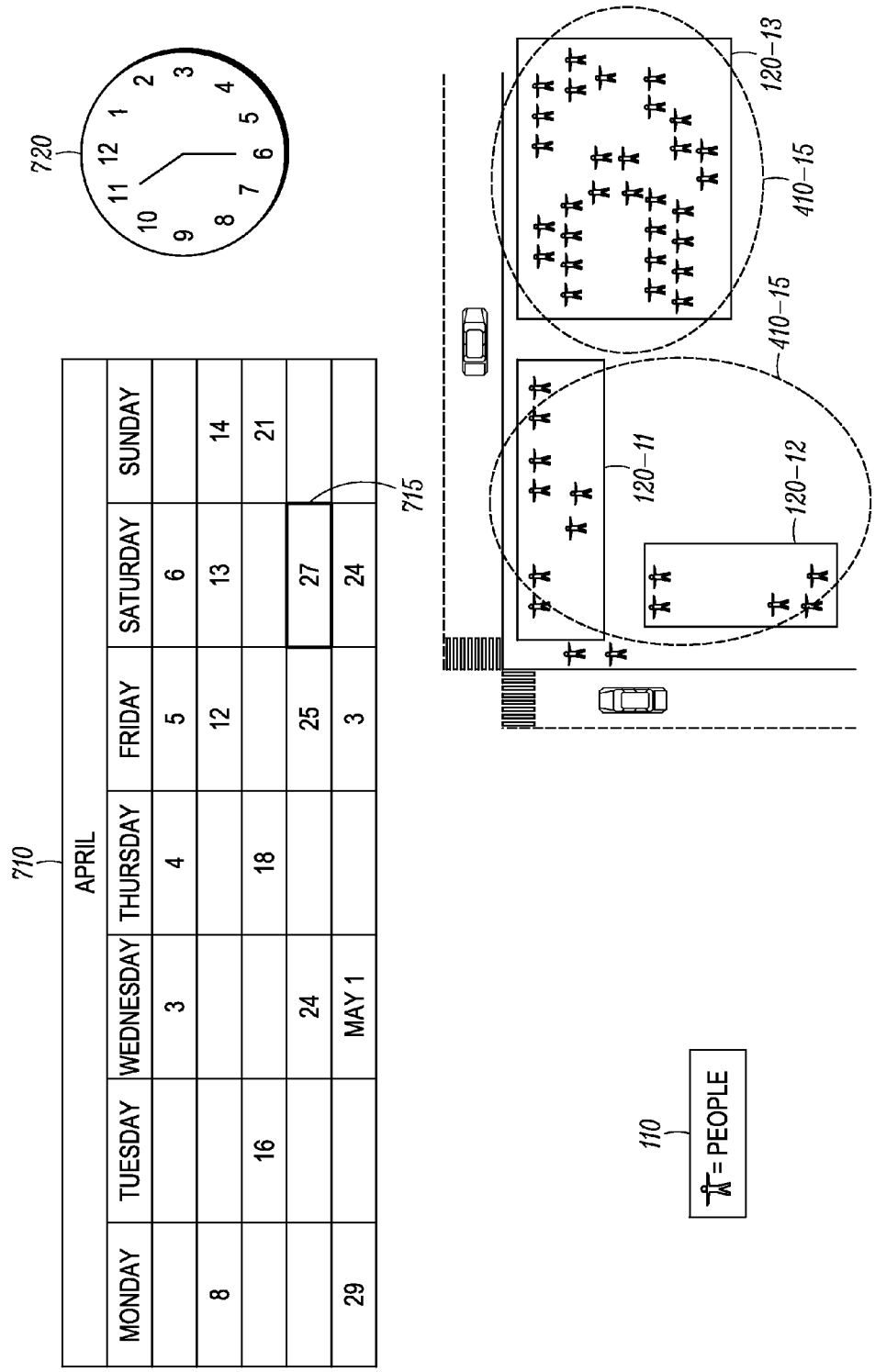
FIG. 7 illustrates changes in population and context characteristics according to changes in a temporal component of a context definition, according to various embodiments of the present disclosure.

In some embodiments, the service provider 230 can determine a difference between a characteristic determined for one context and the characteristic determined at another context. For example, the service provider 230 can compare the median age of people 110 in context 410-14, with the median age of people 110 in context 410-15 shown in FIG. 7. In the specific examples shown in FIGS. 6 and 7, the physical locations 120-11, 120-12, and 120-13 of context 410-14 and context 410-15 are the same. However, the time 720 and date 715 of context 410-15 are different from the time 620 and date 615 of context 410-14. By analyzing the difference in characteristics for each of the contexts, the service provider can determine specific changes or trends. For example, a server computer, based on analysis of sensor data determined to match contexts 410-14 and 410-15, can determine that the average age and the overall attendance increased between April and June of a particular year. While the example shown in FIGS. 6 and 7 refers to two stationary locations, other embodiments of the present disclosure include contexts that are defined by the interior space of multi-person conveyances, such as planes, trains, boats, and buses.

Figure 8:
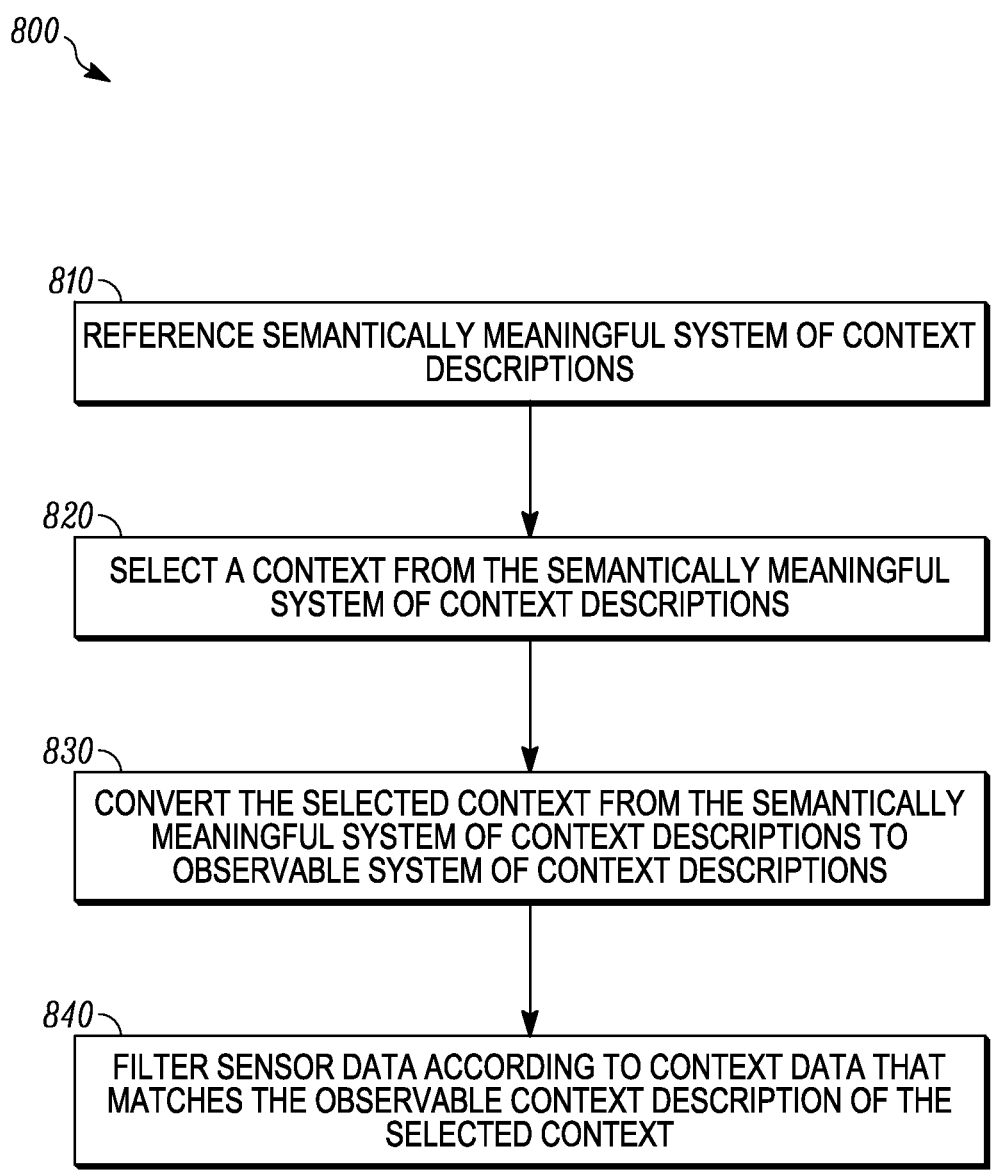
FIG. 8 is a flowchart of a method for defining contexts, according to various embodiments of the present disclosure.

FIG. 8 is a flowchart of a method for determining a particular context and sensor data received from sensor enabled devices for that context. At 810, a service provider 230 can reference a semantically meaningful system of context descriptions. As described herein, a context can be defined by a location, a time period, or a combination thereof. Accordingly, the definition of a context may include a spatial component made in reference to the semantically meaningful system of context descriptions. For example, the context description can reference a map with a layout of predefined locations. The map can represent a municipality with land lots or buildings identified by a system of street addresses or lot numbers. Such municipal maps can include geographical survey data that specifies the metes and bounds of various locations. Semantically meaningful systems of context description can also include maps of individual properties, such as amusement parks, shopping centers, fair grounds, universities, schools, tourist destinations, etc. In such embodiments, a map of an individual property may include absolute or relative positions of features, objects, or amenities on the property. In addition, a semantically meaningful system of context description can also include a temporal component, such as an event calendar or schedule of events. Accordingly, the temporal component can be combined with the spatial component to describe a particular time and a particular location.

In 820, the service provider 230 can select the context from the semantically meaningful system of context descriptions. As discussed above, the selected context can include a temporal and a spatial component. In 830, the service provider 230 may convert the selected context from the semantically meaningful system of context descriptions to an observable system of context descriptions. In such embodiments, the absolute or relative temporal and spatial components of the selected context can be translated into observable spatial components and/or observable temporal components. The observable spatial and temporal components can reference a system that individual sensor enabled electronic devices 210 can observe or sense. For example, the observable spatial components can be defined according to systems for position location determination, e.g., global positioning systems (GPS) or beacon proximity location systems. In one embodiment, a street address for a particular public park can be translated into a set of geographic coordinates that describe the boundaries of the park. Similarly, temporal components can be defined according to a universal or common clock or calendar, such as Greenwich Mean Time (GMT) or the Gregorian calendar. In such embodiments, the name of an event, e.g., a concert can be translated into a period of time that includes a starting time and date and ending time and date along with a particular venue location defined in geographic coordinates. In other embodiments, each individual sensor enabled electronic device 210 can translate the observable spatial and temporal components of the context in which it determines sensor readings into a semantically meaningful system of context descriptions. For example, a sensor enabled smartphone can take an ambient noise reading at a particular set of coordinates as determined by the smartphone's GPS capabilities. The smartphone can then reference an internal map of nearby music venues to determine a particular venue based on the determined coordinate. The smartphone can then associate the ambient noise reading with that venue. In such embodiments, the context data in the sensor data can include the reference to the semantically meaningful system of context descriptions.

In some embodiments, at 840, the service provider 230 can filter sensor data received from multiple sensor enabled electronic devices 210 according the converted context description, i.e., the observable spatial and temporal components of the context description. Accordingly, filtering the sensor data may include determining sensor data that includes context data that matches the converted context description.

On occasion, the sensor data determined to include context data that matches the converted context description may not represent a satisfactory sample size. In such scenarios, various embodiments of the present disclosure can trigger an alert to indicate that the portion of the sensor data determined to match the converted context description is insufficient for determining one or more characteristics for the context. When there appears to be too little sensor data to determine a reliable characteristic for the context, it is possible to increase the sample size by expanding the context definition, e.g., increasing the geographic region and/or time period of the context. If expanding the context definition does not result in a sufficient sample size, but it is also possible to rely on or re-weight explicitly reported context characteristic descriptions. For example, when the sample size of the sensor data is insufficient to interpolate a reliable characteristic, then the interpolated characteristic can be weighted less than any available user reported characteristic data when determining combined characteristic data.

Determination of a Characteristic of a Context

Figure 9:
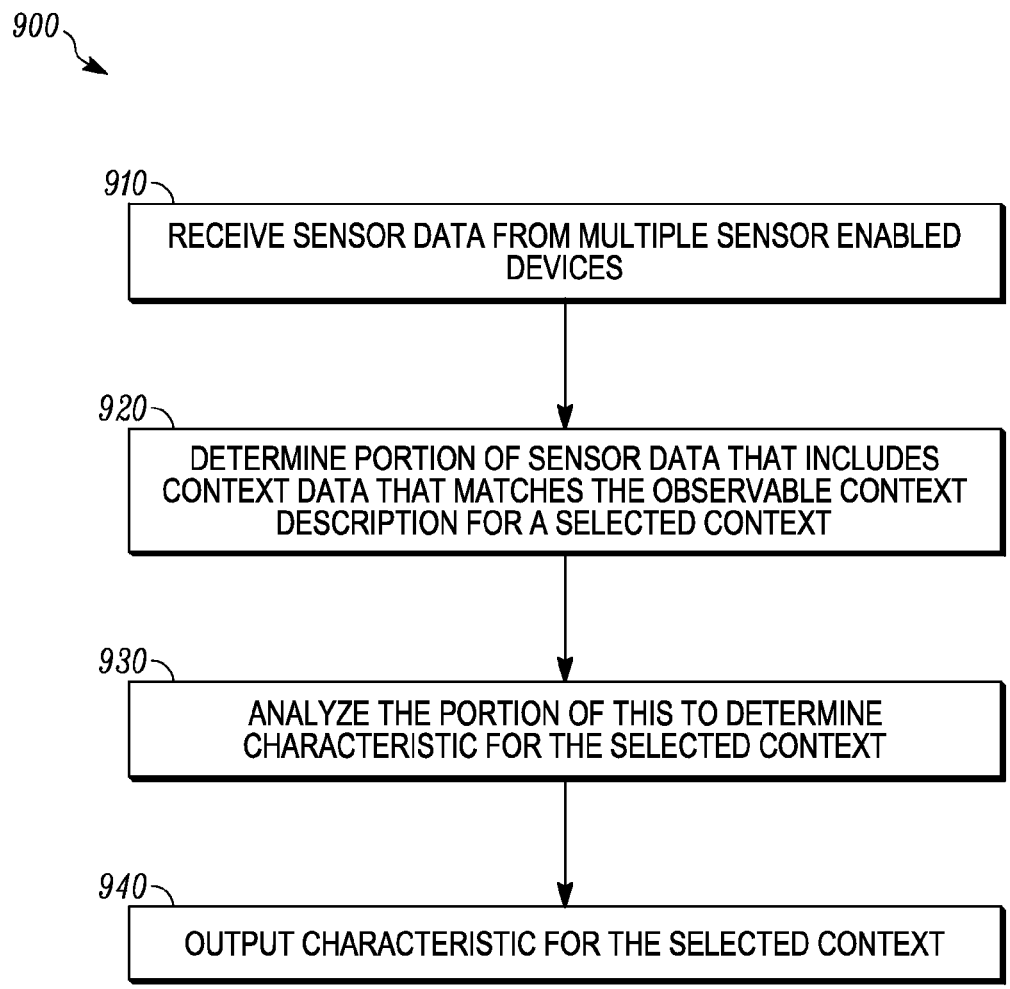
FIG. 9 is a flowchart of a method for determining context characteristics using sensor data received from multiple sensor enabled electronic devices, according to various embodiments of the present disclosure.

Various embodiments of the present disclosure include systems and methods for determining a particular characteristic of a context. For example, FIG. 9 is a flowchart of a method 900 for determining one or more characteristics of a context using sensor data from multiple sensor enabled electronic devices 210. As used herein, the sensor data can include sensor readings as well as user reported data regarding a particular characteristic of interest. In such embodiments, the sensor readings can represent implicit context characteristic descriptions. Also, the user reported data can represent explicit context characteristic descriptions. As shown, method 900 can begin at 910, in which a service provider receives sensor data from multiple sensor enabled electronic devices. The sensor data can include implicit and explicit context characteristic data determined for many different contexts. As discussed above, the sensor enabled electronic devices 210 can include both mobile and stationary electronic devices. At 920, the service provider 230 may determine a portion of the sensor data that includes context data that matches the context description for a particular selected context. In one embodiment, received sensor data can be filtered to find only the sensor that includes context data that indicates that the sensor readings or user reported data was determined while the source sensor enabled electronic devices were in the selected context. In one embodiment, user reported data can also include information and characteristics reported by users using other devices and applications, such a web browser executed on an internet-enable desktop computer or reported to a service provider operator over a land line telephone.

At 930, once the portion of the sensor data associated with the selected context is determined, the sensor readings and/or the user reported data can be analyzed to determine a characteristic of interest for the selected context. Analyzing the sensor data can include mapping the implicit context characteristic indications in the sensor readings to corresponding context characteristics. The mapping from the implicit context characteristic indications to the corresponding characteristics can be predetermined and based on prior analysis performed by the service provider 230. Analyzing the sensor data can also include comparing the mapped corresponding context characteristics with the explicit context characteristic descriptions from the user reported data in the sensor data. When both implicit and explicit context characteristic data are used, the implicit and explicit components can be weighted according to observed or determined reliability of the data. The reliability of the implicit and explicit components can be based on the timeliness, frequency, or consistency of similar sensor data received from each particular sensor enabled electronic device 210. Accordingly, sensor data received from devices that are considered to be more reliable that other devices can be given more weight when determining the context characteristic. Similarly, implicit and explicit components of the context characteristic descriptions can be weighted differently based on perceived reliability. For example, if the sample size of the implicit components is considered to be too small to be reliable, then the explicit components can be given more weight. In contrast, if the explicit components seem to be spurious or inconsistent with other available data, then the implicit components can be given more weight when determining the characteristic of the context.

At 940, once the characteristic or characteristic profile for the selected context is determined, it can be output for use by various users and entities. For example, the form of the output characteristic can include a recommendation or alert regarding the associated context sent to one or more mobile electronic devices. Similarly, the output characteristic for the context can be published to a website, along with other output characteristics for other contexts, or broadcast via email or by RSS. In some embodiments, the output characteristic for the context can include tracking changes or trends of the particular characteristic over a number of context parameters, e.g., over time. Accordingly, changes in the characteristic can be analyzed as a function of a change in context. The change in context can include changes in the temporal and/or spatial components of a particular context. For example, the mood, average age, or wellness of a particular weekly event that may include occasional changes in starting time and venue can be tracked as a function of start time or location. In one embodiment, users can search for contexts with certain characteristics or browse through contexts based on the context and/or the associated characteristics.

Specific examples of context characteristic determination with reference to emotion, demographic, and health characteristics for particular contexts will be discussed in more detail in reference to FIGS. 10 to 17 below.

Determination of an Emotion for a Context

Figure 10:
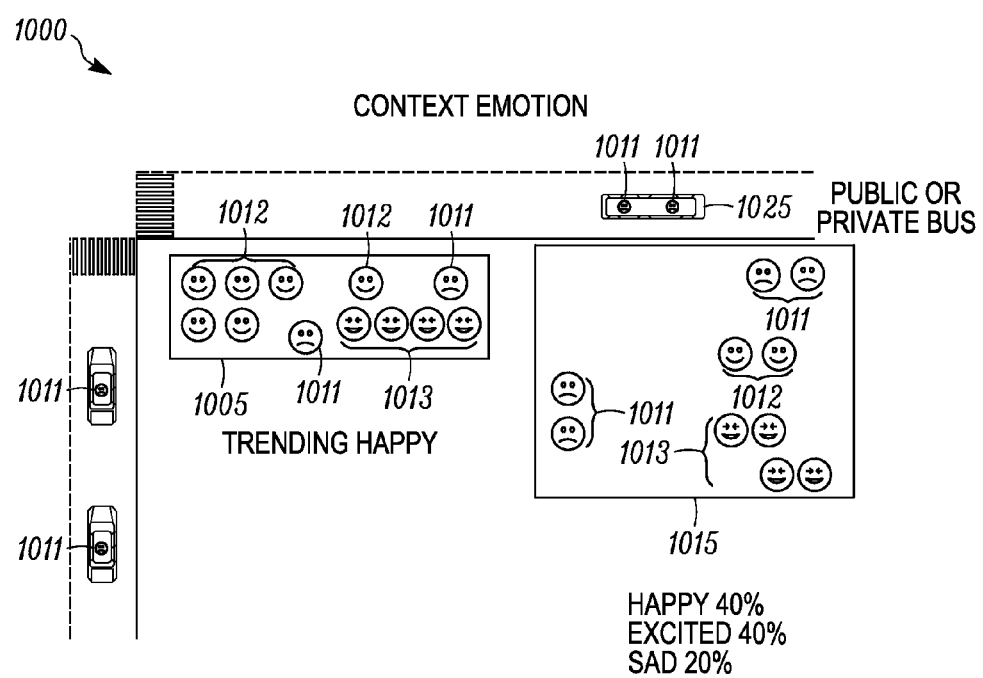
FIG. 10 illustrates emotion sensor data associated with various contexts, according to embodiments of the present disclosure.

Various embodiments of the present disclosure include systems and methods for determining an emotion or emotion profile for particular contexts. FIG. 10 illustrates a scenario 1000 with two stationary location-based contexts 1005 and 1015, and one mobile location-based context 1025, e.g., a public bus. In the particular example shown, context 1005 is a building at the corner of an intersection and context 1015 is another building on the same street. Each of the buildings can be associated with an address or a business name included in a semantically meaningful system of context descriptions. Scenario 1000 also includes a context 1025 defined as the interior of a public or a private bus. In some embodiments, context 1025 can be defined not only as the interior of a particular bus, but as the interiors of some or all buses servicing a particular route or line during some time period of the day.

A service provider 230 may receive emotion sensor data that includes implicit and explicit indications of emotions from sensor enabled devices in any of the contexts 1005, 1015, and/or 1025. The implicit and explicit indications of emotions can be mapped to or represent an emotional characteristic of one or more people in a particular context. Such emotional characteristics can include any number of emotional states, such as happiness, sadness, pensiveness, fear, anger, etc. In the example shown in FIG. 10, the emotion sensor data can include indications of emotions that range from sadness 1011, happiness 1012, and excitement 1013. While this particular example of possible indications of emotions in the emotion sensor data is limited to three indications of various emotions, other embodiments of the present disclosure can include fewer or more possible indications of simple or complex emotions. The level of granularity and range of possible emotions need not be limited.

By analyzing the emotion sensor data for the contexts, the service provider can determine an associated emotion or emotion profile. The style and format of the reported emotion or emotion profile for a particular context can be suited to the needs of the users or other entities that will be using the emotion characterization of the context. For example, when the emotion sensor data associated with context 1005 is analyzed, it can be determined that there are more implicit and/or explicit indications of happiness 1012 and excitement 1013 than indications of sadness 1011. In this particular example, the service provider 230 can determine that the context 1005 is trending as "happy". In another embodiment, when the emotion sensor data associated with context 1015 is analyzed, it can be determined that 40% of the people are happy, 40% of the people are excited, and 20% of the people are sad. Similarly, by analyzing the emotion sensor data associated with context 1025, it can be determined that the general mood of context 1025 is "sad".

In some embodiments, when it is determined that a particular context is associated with a specific emotion, the emotion can be used as an indication that something is occurring or has occurred, or to predict that something is about occur. For example, when context 1025 is determined to be "sad", it can indicate that the bus has experienced a traffic accident or is otherwise experiencing long delays. Similarly, when is determined that all or a majority of the emotion sensor data for a particular context includes indications of happiness, such information can be used as an indication that something has gone favorably, e.g., a successful event is occurring. While characterizations of the emotion for a context that includes static or one time summaries are useful for some purposes, it is often useful to also include analysis of the changes in the emotion or emotion profile for a context over one or more spatial or temporal components of the context.

Figure 11:
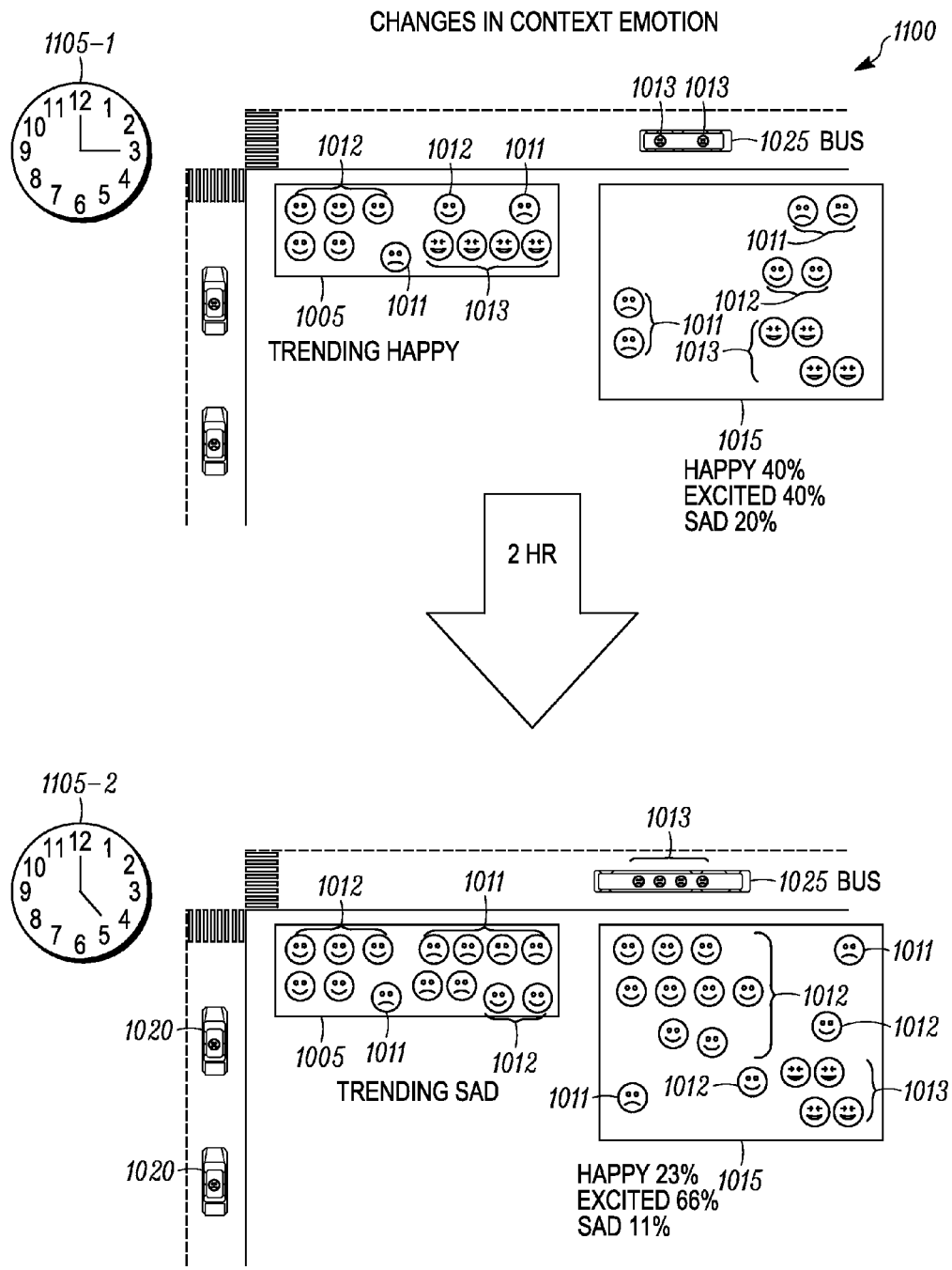
FIG. 11 illustrates tracking changes in a motion sensor data associated with various contexts, according to embodiments of the present disclosure.

For example, FIG. 11 illustrates a scenario 1100 in which trends or changes in the emotion sensor data can be observed. As shown, at time 1105-1, the emotions for contexts 1005, 1015, and 1025 can be characterized as shown in FIG. 11. However, after some amount of time, e.g., 2 hours, at time 1105-2, the emotion sensor data received from various sensor enabled electronic devices 210 in context 1005 can be analyzed to determine that the context is trending "sad". This is because additional indications of a sad emotion have been received in the last 2 hours. Also, at time 1105-2, the emotion sensor data from devices determined to be in context 1015 can be analyzed to determine that the context is 23% "happy", 66% "excited", and 11% "sad". In reference to the context of the bus line or route 1025, the emotion sensor data can be analyzed to determine that people on the bus are generally happy. The changes in the emotions or emotion profiles for the contexts 1005, 1015, and 1025 can be tracked and the changes or the trends can be included in the output regarding emotion or emotion profile for each context. For example, a some particular time, context 1005 may be characterized as "sad" but, based on the recent trends in the emotion sensor data for the context, it may be experiencing a change in the predominate mood from sad and trending toward "happy".

While trends in context emotion over time are useful for some analysis, some embodiments include determining trends in context emotion according to changes in physical location. For example, context 1025 of the bus can include not only the interior of the bus, but can also include environments through which the bus travels. Accordingly, trends in emotion can be tracked over changes in the buses position along its route. For example, the emotion of the bus context 1025 can change from "happy" while the bus is traveling through a nice part of town with little traffic to "sad" when the bus starts traveling through another part of town with heavy traffic. Other aspects of the context 1025 of the bus can also be tracked. For example, changes in drivers, operators, tour guides, ambient music, dynamic advertising (video screen monitors or public announcements), lighting, cleanliness, speed of travel, style of driving, condition of the road, etc. can all be included in the context 1025 and cross-referenced with the emotion sensor data received from the sensor enabled electronic devices to determine the impact of such individual and combined changes on the mood of the context. In particular example shown in FIG. 11, the bus context 1025 has been described in detail, however other multi-person conveyances and transportation routes can also be used to define a particular context. For example, other contexts can include stretches of freeway, airline routes, train routes, subway lines, sections of road, etc. for which emotion sensor data can be analyzed to determine an associated emotion or an emotion profile.

Figure 12:
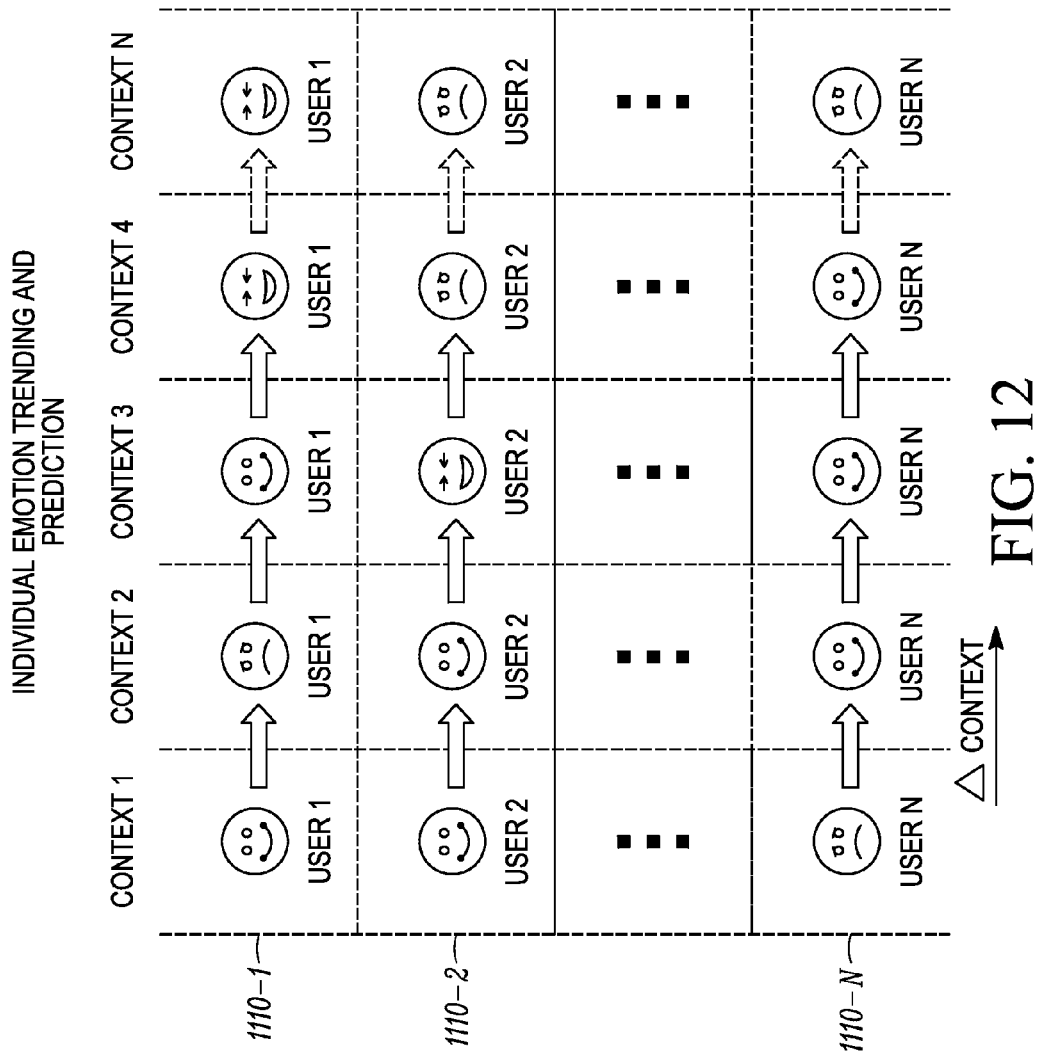
FIG. 12 illustrates trends of individual user emotion based on changes in context, according to embodiments of the present disclosure.

Other embodiments of the present disclosure include tracking trends in emotion for individual users. In such embodiments, sensor enabled mobile electronic devices 210 can be associated with particular users. Emotion sensor data, and other sensor data, received from such devices can also be associated with individual users. As a user moves from one context to the next context, changes in that user's emotion can be tracked. For example, FIG. 12 shows emotion trend profiles 1110 that track the emotional changes for individual users 110 as they move from one context to another. As shown, profile 1110-1 tracks the emotion or mood of a user 1 as he or she goes from context to context. Once some amount of emotion sensor data for a particular user 1 in a variety of contexts is collected, various embodiments of the present disclosure can begin predicting how a user's mood will change if he or she goes from one particular context to another particular context.

Figure 13:
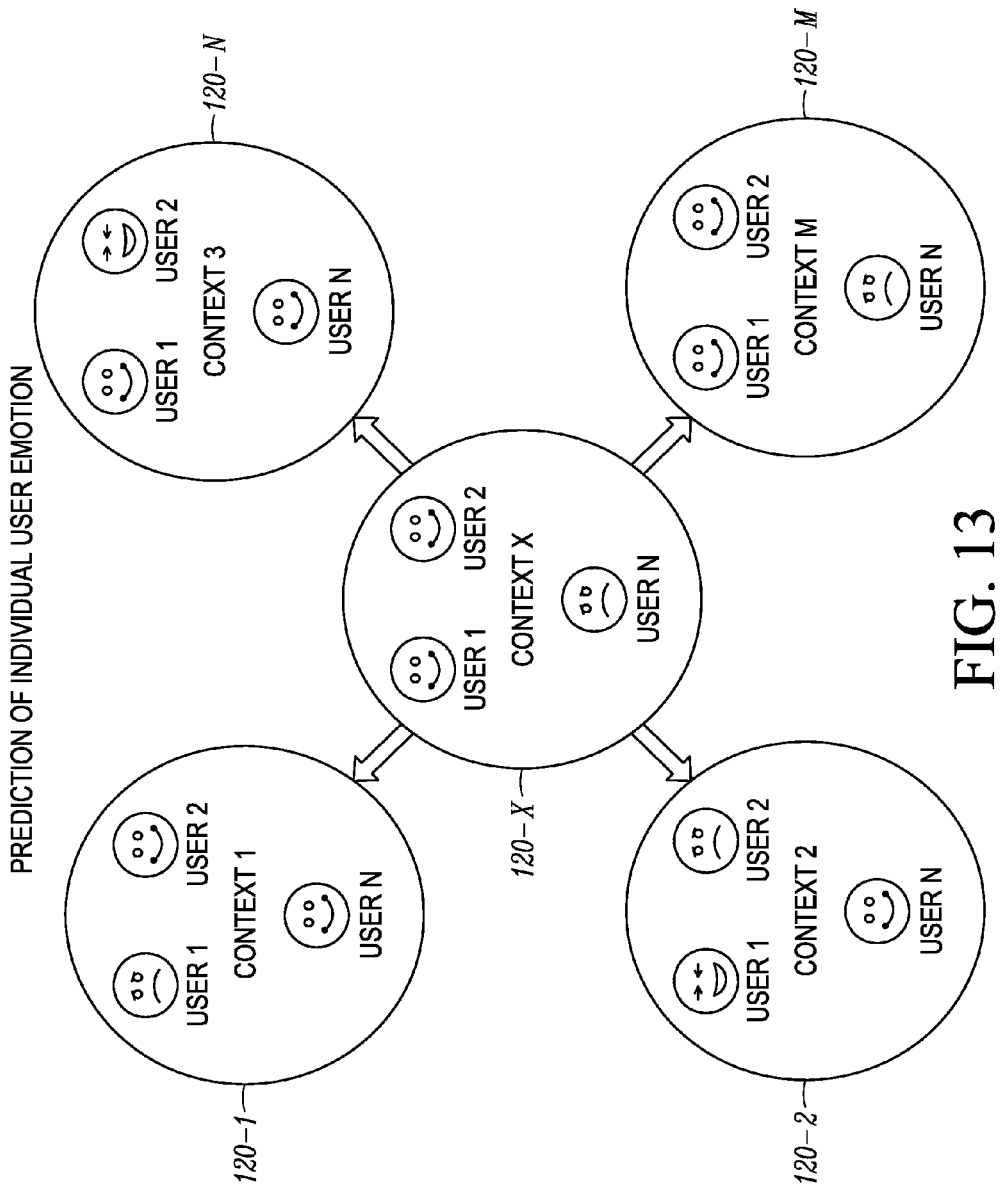
FIG. 13 prediction of individual user emotions based on changes in context, according to embodiments of the present disclosure.

FIG. 13 illustrates embodiments of the present disclosure can reference the emotion trend profiles 1110 to predict a change in emotion for individual users in various scenarios as they move from one type of contexts to another type of context. Based on the emotion trend profile 1110 for each individual user, various predictions about the change in a user's mood are represented according to shifts in context from a starting context 120-X. If one particular user moves from starting context 120-X to another context, such as 120-1, then, based on the emotion trend profile 1110 for that user, it can be predicted that the user's mood will change or stay the same. In the example shown, various users who begin as being happy in context 120-X can be predicted to remain happy, become excited, or be saddened when moved into one of the other contexts 120. Similarly, a user who begins as being sad in context 120-X can be predicted to remain sad, or become happy or excited when moved into one of the other contexts 120.

In some embodiments, the prediction of a particular change in a user's mood can include consideration of current or historic determinations of the emotion of the context into which the user is about to enter. For example, a prediction can be made about whether a particular user will be happy if he or she attends a particular event at a particular entertainment venue that is typically lively and happy. If trends in the user's profile 1110 indicate a favorable mood change when going into such a context, then a prediction can be made that the user will enjoy the change in context. Based on such predictions, recommendations and/or alerts can be sent to the user via his or her associated sensor enabled mobile electronic device 210 when it is determined that the user is within some proximity to particular context.

Determination of Context Demographics

Figure 14:
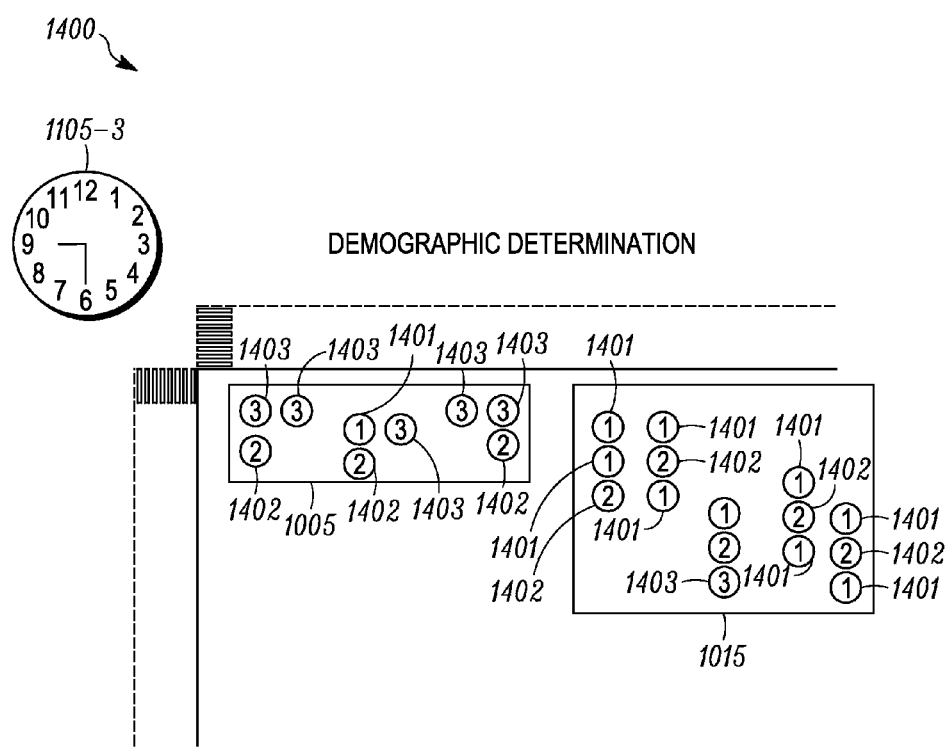
FIG. 14 illustrates demographic sensor data associated with various contexts, according to embodiments of the present disclosure.

Various users and entities often find it useful to know about the demographics of a particular context. Using demographic sensor data that can include implicit and explicit indications of various demographic characteristics of people and environments in particular contexts, various embodiments of the present disclosure can determine a demographic or demographic profile for the contexts. For example, FIG. 14 illustrates contexts 1005 and 1015 that include a spatial component, e.g., an address, and a time component 1105-3, for which demographic sensor data has been received and/or collected. The demographic sensor data can include indications of demographic characteristics for people within each of the contexts. For the sake of clarity, the number of implicit and explicit indications of demographic characteristics shown in FIG. 14 has been limited. As shown, the demographic sensor data can include indications of a first demographic characteristic 1401, a second demographic characteristic 1402, and a third demographic characteristic 1403. While described generically as individually numbered demographic characteristics, such demographic characteristics can include any individual demographic characteristic or combination of demographic characteristics. For example, the individually numbered demographic characteristics 1401, 1402, and 1403 can represent any combination of quantifiable statistics for the people, such as age, sex, ethnicity, race, sexual preference, social class, social scene, and any other implicitly or explicitly determinable association with a particular group or classification.

By filtering the demographic sensor data determined to include or be associated with context data that matches spatial and/or temporal components of contexts 1005 and 1015, various embodiments of the present disclosure can determine demographic profiles for each context. The demographic profile for the context can include a complete listing of the available demographic details for each person in that context. If less granularity is required or desired, then a summary demographic profile can be created. For example, based on the demographic sensor data, it can be determined that the demographics of context 1005 are predominantly male. Similarly, it can be determined that the demographics of context 1015 are predominantly female with an average age greater than 55. The demographic profile for a particular context can then be output over various communication channels, e.g., published to a website, sent to groups of subscribing users via email or Short Message Service (SMS), or pushed to an application executed by mobile electronic device.

Figure 15:
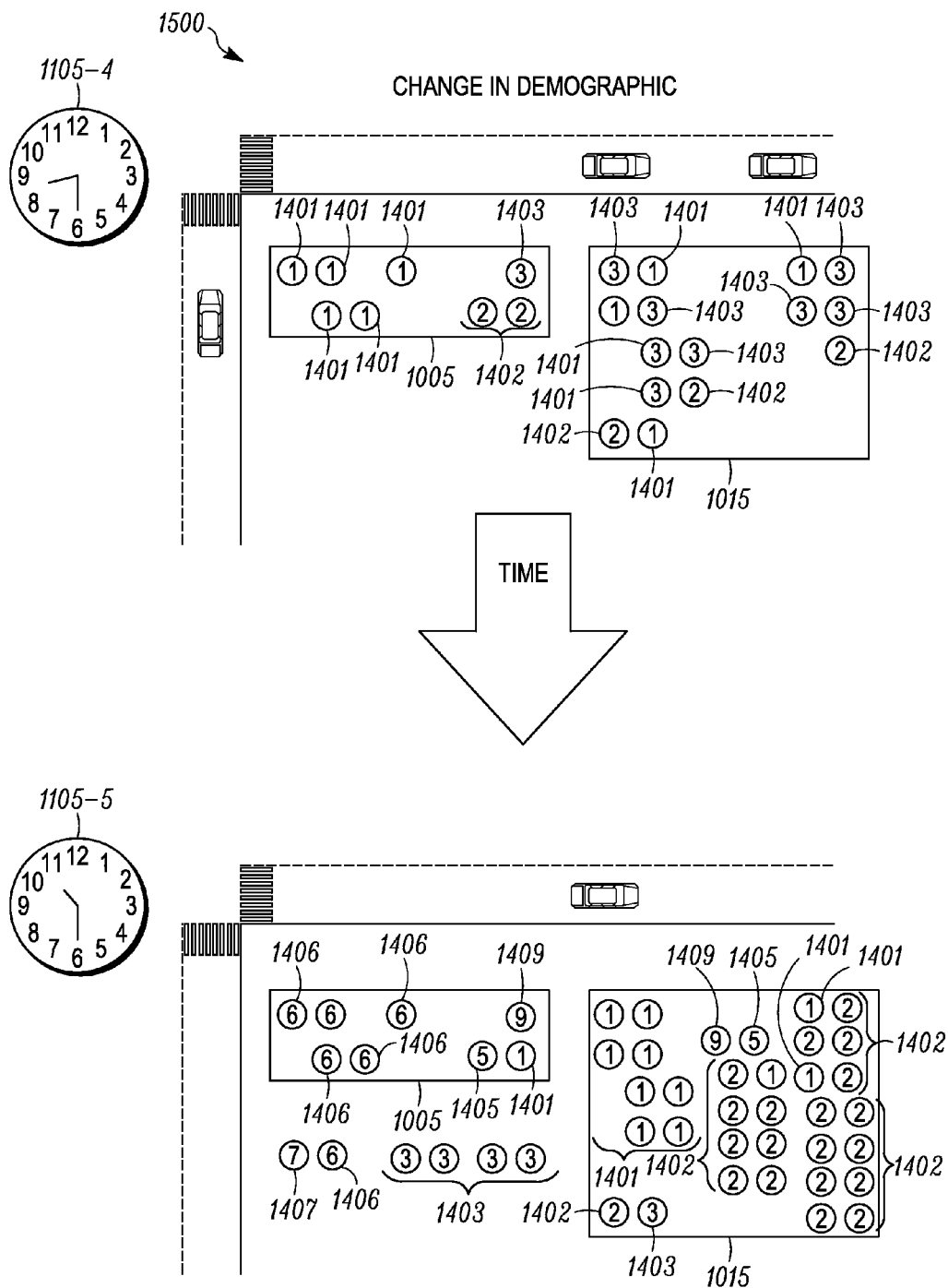
FIG. 15 illustrates changes in demographic sensor data associated with various contexts, according to various embodiments of the present disclosure

Just as it is often useful to track changes in the emotion for a context, it can also be useful to track changes in demographics for a context. FIG. 15 illustrates a scenario 1500, in which changes in the demographic profile of contexts 1005 and 1015 are observed from time 1105-4 to time 1105-5. As shown, context 1005, e.g., the interior and exterior region around a bar at a particular intersection, begins at time 1105-4 being predominantly associated with demographic sensor data that includes a particular demographic characteristic 1401. For example, demographic characteristic 1401 can be an indication of a male over the age of 40. Similarly, context 1015 at time 1105-4 can be determined to be associated primarily with demographic sensor data that includes indications of the particular demographic characteristic 1403, e.g., females around the age of 25. After some time period, at time 1105-5, the demographics of contexts 1005 and 1015 may change. As illustrated, context 1005 may now also be associated with demographic sensor data that includes various instances of demographic characteristics 1401, 1403, 1405, 1406, 1407, and 1409. The demographic sensor data of context 1015 at time 1105-5 can shift to include a predominant mixture of demographic characteristic 1401 and 1402. Such shifts can indicate a change in the age, sex, ethnicity, or other demographic characteristic of the inhabitants or patrons of a particular context, i.e. the building or a business. The changes or trends in the demographic or demographic profile of a context can then also be associated with the context and output over various communication channels.

Determination of Health and Wellness of a Context

Figure 16:
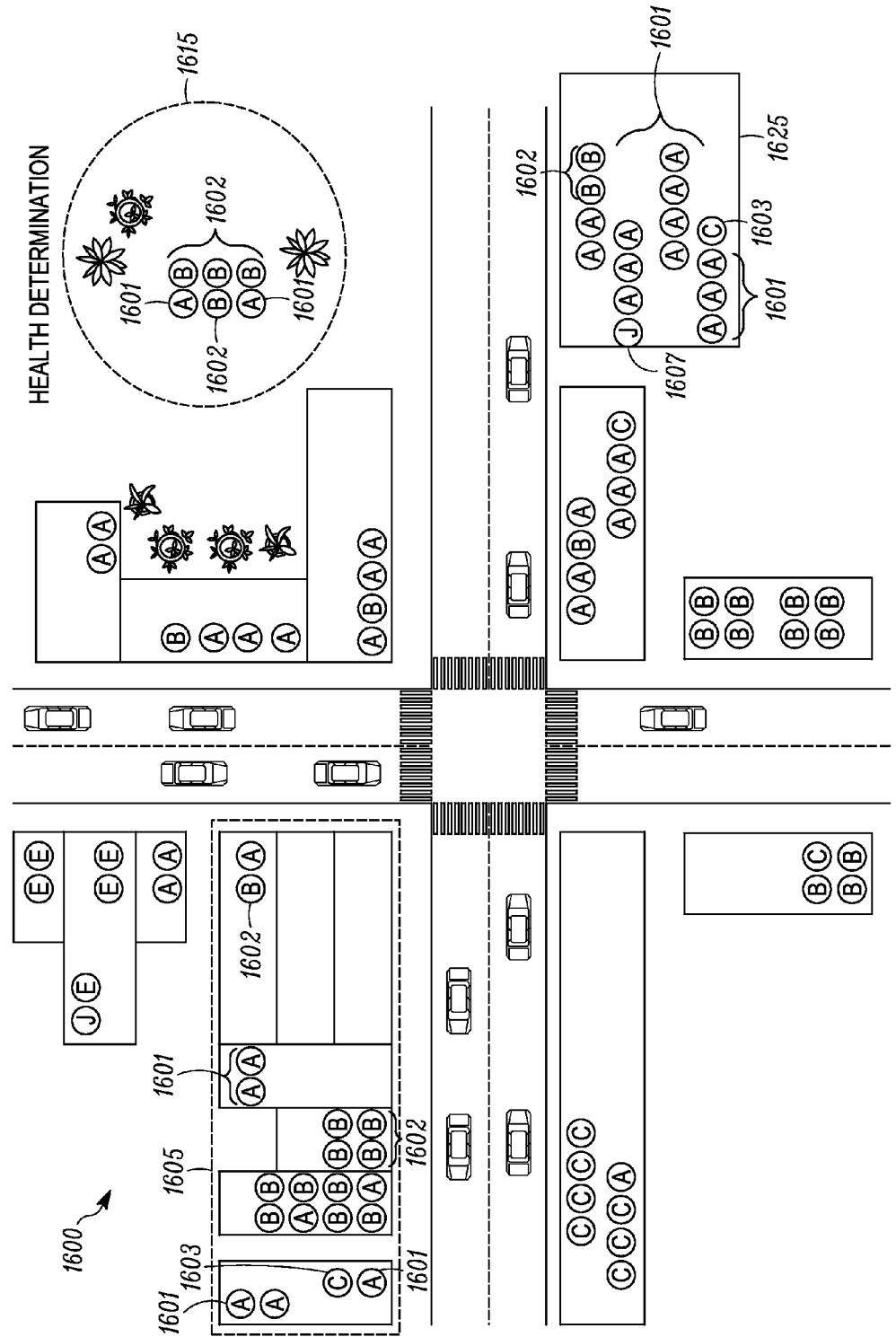
FIG. 16 illustrates health sensor data associated with various contexts, according to embodiments of the present disclosure.
Figure 17:
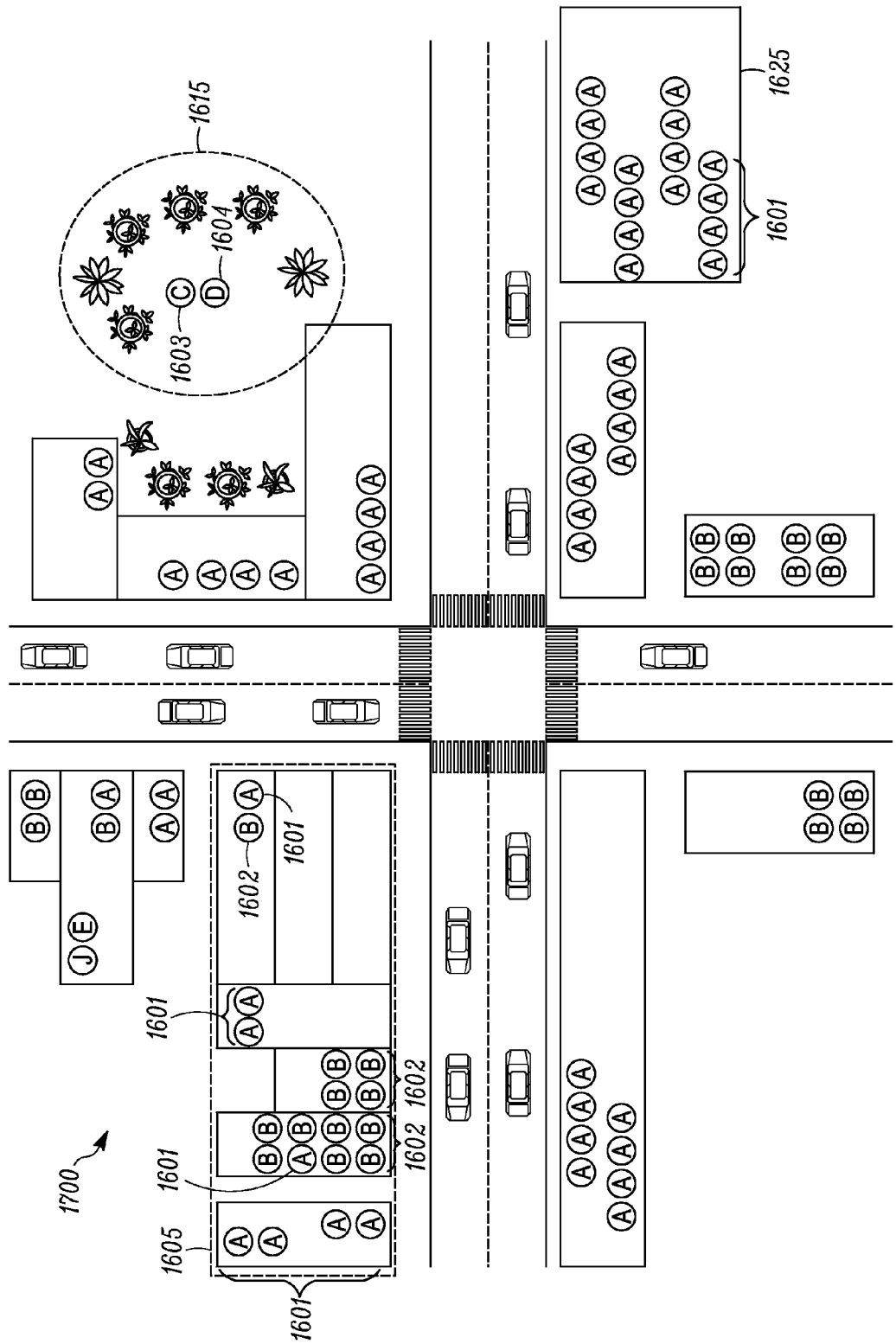
FIG. 17 illustrates changes in health sensor data associated with various contexts, according to embodiments of the present disclosure.

Through the use of various types of individual and group health sensors, various embodiments of the present disclosure can determine the health and wellness for various contexts. FIGS. 16 and 17 illustrate two scenarios 1600 and 1700 of the same geographic region, e.g., a part of a town or city that includes a number of contexts. The contexts can include the group of buildings in context 1605, an outdoor park in context 1615, and a particular building in context 1625 during some particular time period, e.g., a week, month, or year. Accordingly, scenario 1600 in FIG. 16 can be associated with one particular time period and scenario 1700 in FIG. 17 can be associated with another particular time period. The time periods can overlap or be mutually exclusive.

By using the addresses, lot numbers, and/or the corresponding GPS coordinates of the locations located in contexts of scenario 1600 to define the contexts, various embodiments can filter health sensor data received from multiple sensor enabled electronic devices 210 to determine the health sensor data that includes context data that matches or is associated with the contexts of interest. The health sensor data determined to include context data that matches each context can then be analyzed to determine a health profile for the corresponding context.

Health sensor data received from health sensor enabled devices throughout scenario 1600 can be filtered to determine data that is associated with contexts 1615 and 1625, and any other area or region or time frame that a user or entity might be interested in as an individual or composite context. For example, context 1605 can be defined by the areas in and around the buildings associated with a particular range of addresses. The range of addresses can be used to determine the specific coordinates of the geographic regions occupied by the buildings by referencing a geographic map or a third-party mapping service. Context 1615 can be defined by the name of the park, which can be used to reference some system of context descriptions, such as municipal survey data, that defines the metes and bounds of the park with respect to geographical coordinates. Context 1625 can be defined by the block and lot number of the building or the name of the business that uses the building in context 1625. Such semantically meaningful systems of context descriptions can then reference an observable system of context descriptions to determine the limits of each context that will be observable by sensor enabled devices. As with other embodiments of the present disclosure, health sensor enabled devices can include GPS, proximity-based, and other location determination and time determination capabilities. Accordingly, any health sensor readings obtained by the health sensor enabled devices can be associated with context data that indicates the contexts in which the health sensor readings were captured.

The health profiles for contexts 1605, 1615, and 1625 can include various details about the health sensor data determined by health sensor enabled devices while the devices were within each context. For example, the health profile for contexts 1605, 1615, and 1625 can include a complete listing of all implicit health sensor data and explicit user reported health data, such as health indications 1601, 1602, and 1603. In other embodiments, health profiles can include a summary or average of the health indications present in the sensor data for a particular context 1605. In general, the health profile for each context can be customized to analyze the health indications according to the needs of a particular entity or user.

While the health indications 1601, 1602, and 1603 are listed as generic indications or descriptors of health of one or more people within the context, e.g., A, B, and C, embodiments of the present disclosure include any and all health and/or wellness descriptors determinable, observable, or inferable by health sensor enabled devices. For example, descriptors of health can include a description of body mass index (BMI), weight, blood pressure, blood sugar, heart rate, temperature, stress, or body fat content. Such descriptions can include numerical indexes or general/layman terms, such as underweight, normal weight, overweight, obese, and morbidly obese. Other descriptors of health can include explicit user reported data, such as vaccination status, mental health status, feelings of wellness, disease and health history, etc. In some embodiments, the health sensor data can also include environmental sensor readings that describe or indicate the presence of toxins, poisons, pollution, and other helpful or harmful factors that can impact the health of individuals that inhabit or use a particular context.

Accordingly, the health descriptors from the health sensor data associated with a context can be analyzed to produce default or custom health profiles for that context. For example, context 1625 can include a restaurant. The summary of the health sensor data that includes health indications 1601, 1602, 1603, and 1607, can be included in the health profile of the restaurant, e.g., overweight people eat at the restaurant. Similarly, the health profile associated with context 1615, that includes outdoor park space, can indicate that people who use the park are generally physically fit and have low cholesterol.

While snapshot or cumulative health profiles for each context can be useful for various purposes, is often useful to also track the changes in health profiles and/or health descriptors for specific contexts according to spatial or temporal changes. As discussed above in reference to emotion and demographic changes for specific contexts, embodiments of the present disclosure can also track changes in health for contexts. For example, scenario 1700 of FIG. 17 illustrates changes in health for contexts 1605, 1615, and 1625 relative to scenario 1600 of FIG. 16. Specifically, the health profile associated with context 1605 may change only slightly, if at all, if only limited changes in the associated health descriptors in the health sensor data are observed between scenario 1600 and 1700. Meanwhile, the health profiles associated with context 1615 and 1625 may change dramatically due to the observed or determined differences in health descriptors in the health sensor data associated with those contexts. Whereas the health profile associated with context 1615 in scenario 1600 may have indicated that physically fit people frequented the park, the health profile associated with the context 1615 in scenario 1700 may indicate that the park is now frequented by people who smoke cigarettes or drink alcohol on a regular basis. In contrast to the apparent decline in the health of context 1615, the health profile of the restaurant in context 1625 may change for the better. For example, the health indicators 1601 associated with context 1625 in scenario 1700 may now indicate that mostly physically fit people with low blood pressure patronize the restaurant.

As with other characteristic profiles, the health profiles of the various contexts can be output over various communication channels and methods. For example, the health profile for the particular restaurant in context 1625 can be included in a restaurant review. Outputting the health profile for the context 1605 that includes a number of buildings in a particular neighborhood can include generating a recommendation or an alert to real estate agents or public health department officials that the health for the context is in decline or is improving. Health profiles that indicate a decline or an increase in the general health or specific health characteristics of individuals who inhabit or use particular contexts can be used to indicate, analyze, and predict various environmental changes, epidemic changes, population changes, and other changes occurring within a context.

Particular embodiments may be implemented in a non-transitory computer-readable storage medium for use by or in connection with the instruction execution system, apparatus, system, or machine. The computer-readable storage medium contains instructions for controlling a computer system to perform a method described by particular embodiments. The computer system may include one or more computing devices. The instructions, when executed by one or more computer processors, may be operable to perform that which is described in particular embodiments.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The above description illustrates various embodiments along with examples of how aspects of particular embodiments may be implemented. The above examples and embodiments should not be deemed to be the only embodiments, and are presented to illustrate the flexibility and advantages of particular embodiments as defined by the following claims. Based on the above disclosure and the following claims, other arrangements, embodiments, implementations and equivalents may be employed without departing from the scope hereof as defined by the claims.

What is claimed is:

1. A method comprising:
    receiving, by a computer system, emotion sensor data for a plurality of contexts from a plurality of distributed electronic devices, wherein each of the plurality of contexts corresponds to one or more of a geographical area and a time period, wherein the emotion sensor data comprises implicit emotion indicators based on information sensed by the plurality of distributed electronic devices for the plurality of contexts, wherein the emotion sensor data further comprises explicit emotion descriptors based on user reported descriptions of emotions for the plurality of contexts;
    determining, by the computer system, a first context in the plurality of contexts;
    determining, by the computer system, a first portion of the emotion sensor data determined to be received from a first portion of the plurality of distributed electronic devices, wherein the first portion of the emotion sensor data is based on information sensed for the first context;
    generating, by the computer system, a first emotion profile for the first context based on the first portion of the emotion sensor data, the generating comprising weighting the implicit emotion indicators differently from the explicit emotion descriptors based at least on a reliability,
    tracking, using an emotion trend profile, an emotional change associated with a move from one of the plurality of contexts to another of the plurality of contexts; and
    predicting, using the emotion trend profile and the first emotion profile, a predicted emotional change associated with a move from one of the plurality of contexts to the first context;
    wherein the first emotion profile comprises a description of a first emotion associated with the first context, and wherein the computer system comprises one or more computer processors configured to perform the steps of the method.

2. The method of claim 1, wherein the first portion of the emotion sensor data comprises a plurality of emotion sensor readings from information sensed by the first portion of the plurality of distributed electronic devices, wherein the plurality of emotion sensor readings include an emotion indicator for a plurality of people associated with the first context.

3. The method of claim 1, wherein the plurality of distributed electronic devices comprises a plurality of mobile electronic devices.

4. The method of claim 3, wherein the plurality of distributed electronic devices further comprises a plurality of stationary electronic devices configured to sense emotional data for a plurality of particular locations.

5. The method of claim 4, wherein the first portion of the plurality of distributed electronic devices comprises a portion of the plurality of mobile electronic devices and a portion of the plurality of stationary electronic devices.

6. The method of claim 5, wherein emotion sensor data determined to be received from the plurality of mobile electronic devices is weighted differently from emotion sensor data determined to be received from the plurality of stationary electronic devices in generating the first emotion profile.

7. The method of claim 1, further comprising:
    determining, by the computer system, a second context in the plurality of contexts;
    determining, by the computer system, a second portion of the emotion sensor data determined to be received from a second portion of the plurality of distributed electronic devices; and
    generating, by the computer system, a second emotion profile for the second context based on the second portion of the emotion sensor data,
    wherein the second emotion profile comprises a description of a second emotion associated with the second context.

8. The method of claim 7, wherein the first context comprises a first time period during an event, and the second context comprises a second time period during the event.

9. The method of claim 7, wherein the first context comprises a first location, and the second context comprises a second location.

10. The method of claim 7, further comprising:
    determining, by the computer system, a difference between the first emotion profile and the second emotion profile, wherein in the difference between the first emotion profile and the second emotion profile describes an emotion profile trend related to the first context and the second context; and outputting, by the computer system, the difference between the first emotion profile and the second emotion profile.

11. The method of claim 7, wherein the second portion of the plurality of distributed electronic devices is determined from the first portion of the plurality of distributed electronic devices.

12. The method of claim 11, wherein the first context comprises a first location, and the second context comprises a second location, and wherein a portion of the first location comprises the second location.

13. The method of claim 1, wherein the first context comprises event data at which the first portion of the plurality of distributed electronic devices were present to sense the information on which the emotion sensor data is based.

14. The method of claim 13, wherein the event data comprises a particular time period associated with a particular location.

15. The method of claim 1, wherein the first context comprises a dynamically determined geographical region in which the first portion of the plurality of distributed electronic devices were located to sense the information on which the emotion sensor data is based.

16. The method of claim 1, further comprising receiving, by the computer system, event calendar data, wherein the event calendar data comprises a plurality of dates and a plurality of associated locations, and wherein determining the first context comprises referencing the event calendar data.

17. The method of claim 1, further comprising outputting, by the computer system, the first emotion profile.

18. A non-transitory computer-readable storage medium containing instructions that, when executed, control one or more computer processors of an electronic device to be configured for:
  receiving emotion sensor data from a plurality of distributed electronic devices for a plurality of contexts, wherein each of the plurality of contexts corresponds to one or more of a geographical area and a time period, wherein the emotion sensor data comprises implicit emotion indicators based on information sensed by the plurality of distributed electronic devices for a plurality of contexts, and wherein the emotion sensor data further comprises explicit emotion descriptors based on user reported descriptions of emotions for the plurality of contexts;
  determining a first context in the plurality of contexts;
  determining a first portion of the emotion sensor data determined to be received from a first portion of the plurality of distributed electronic devices, wherein the first portion of the emotion sensor data is based on information sensed for the first context;
  generating a first emotion profile for the first context based on the first portion of the emotion sensor data, the generating comprising weighting the implicit emotion indicators differently from the explicit emotion descriptors based at least on a reliability,
  tracking, using an emotion trend profile, an emotional change associated with a move from one of the plurality of contexts to another of the plurality of contexts; and
  predicting, using the emotion trend profile and the first emotion profile, a predicted emotional change associated with a move from one of the plurality of contexts to the first context;
  wherein the first emotion profile comprises a description of an emotion associated with the first context.

19. An electronic device comprising:
  at least one computer processor;
  an emotion sensor communicatively coupled to the at least one computer processor;
  an electronic communication interface communicatively coupled to the at least one computer processor; and
  a non-transitory computer-readable storage medium containing instructions, that when executed, control the at least one computer processor to be configured to:
  activate the emotion sensor to determine an emotion sensor reading;
  determine context data for the emotion sensor reading, wherein the context data describes circumstances in which the emotion sensor reading was determined;
  generate emotion sensor data comprising implicit emotion indicators based on the context data and the emotion sensor reading;
  track, using an emotion trend profile, an emotional change associated with a move from one of the plurality of contexts to another of the plurality of contexts;
  predict, using the emotion trend profile and the first emotion profile, a predicted emotional change associated with a move from one of the plurality of contexts to the first context;
  send the emotion sensor data to one or more remote service providers through the electronic communication interface; and
  receive, from a first remote service provider in the one or more remote service providers through the electronic communication interface, summary emotion sensor data for a particular context, wherein the particular context corresponds to one or more of a geographical area and a time period, wherein the summary emotion sensor data comprises emotion sensor data for the particular context that has been received by the first remote service provider from a plurality of other electronic devices, wherein the summary emotion sensor data further comprises explicit emotion descriptors based on user reported descriptions of emotions for the plurality of contexts, wherein the implicit emotion indicators are weighted differently from the explicit emotion descriptors based at least on a determination of reliability, and wherein the summary emotion sensor data is determined to include context data that matches the particular context.

* * * * *